United States Patent
Ravetch et al.

(10) Patent No.: US 11,760,805 B2
(45) Date of Patent: *Sep. 19, 2023

(54) ANTIBODIES TO CD40 WITH ENHANCED AGONIST ACTIVITY

(71) Applicant: The Rockefeller University, New York, NY (US)

(72) Inventors: Jeffrey V. Ravetch, New York, NY (US); Rony Dahan, New York, NY (US)

(73) Assignee: THE ROCKEFELLER UNIVERSITY, New York, NY (US)

(*) Notice: Subject to any disclaimer, the term of this patent is extended or adjusted under 35 U.S.C. 154(b) by 91 days.

This patent is subject to a terminal disclaimer.

(21) Appl. No.: 17/150,008

(22) Filed: Jan. 15, 2021

(65) Prior Publication Data
US 2021/0139598 A1    May 13, 2021

Related U.S. Application Data

(63) Continuation of application No. 15/195,119, filed on Jun. 28, 2016, now Pat. No. 10,894,835.

(60) Provisional application No. 62/304,012, filed on Mar. 4, 2016.

(51) Int. Cl.
| | |
|---|---|
| C07H 21/04 | (2006.01) |
| C12P 21/06 | (2006.01) |
| C12N 1/20 | (2006.01) |
| C12P 5/02 | (2006.01) |
| C12N 5/20 | (2006.01) |
| C12N 15/00 | (2006.01) |
| C07K 16/28 | (2006.01) |
| A61K 39/00 | (2006.01) |

(52) U.S. Cl.
CPC .... *C07K 16/2878* (2013.01); *A61K 2039/505* (2013.01); *C07K 2317/21* (2013.01); *C07K 2317/51* (2013.01); *C07K 2317/515* (2013.01); *C07K 2317/52* (2013.01); *C07K 2317/522* (2013.01); *C07K 2317/524* (2013.01); *C07K 2317/72* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,338,660 B2 | 3/2008 | Bedian et al. | |
| 7,626,012 B2 | 12/2009 | Bedian et al. | |
| 10,479,838 B2* | 11/2019 | Ravetch | A61P 35/00 |
| 2004/0110226 A1 | 6/2004 | Lazar et al. | |
| 2009/0074711 A1 | 3/2009 | Glennie | |
| 2014/0010812 A1 | 1/2014 | Ravetch et al. | |

FOREIGN PATENT DOCUMENTS

| | | | | |
|---|---|---|---|---|
| JP | 2018526978 A | 9/2018 | | |
| WO | 2003/040170 A2 | 5/2003 | | |
| WO | 2012087928 A2 | 6/2012 | | |
| WO | WO-2014070934 A1 * | 5/2014 | .............. | A61P 29/00 |
| WO | 2014106015 A2 | 7/2014 | | |
| WO | 2015070972 A1 | 5/2015 | | |
| WO | 2016028810 A1 | 2/2016 | | |
| WO | 2017004006 A1 | 1/2017 | | |

OTHER PUBLICATIONS

Bjorck et al. The CD40 agonistic monoclonal antibody APX005M has potent immune stimulatory capabilities. Journal for ImmunoTherapy of Cancer 2015, 3(Suppl 2):P198. (Year: 2015).*
Richman et al. Anti-human CD40 monoclonal antibody therapy is potent without FcR crosslinking. OncoImmunology 3, e28610; Apr. 2014. (Year: 2014).*
Dahan et al., "Therapeutic Activity of Agonistic, Human Anti-CD40 Monoclonal Antibodies Requires Selective FcγR Engagement," Cancer Cell ((2016); 29:820-831.
MacCallum et al., "Antibody-antigen Interactions: Contact Analysis and Binding Site Topography," J. Mol. Biol. (1996); 262:732-745.
Rudikoff et al., "Single amino acid substitution altering antigen-binding specificity," Proc. Natl. Acad. Sci. (Mar. 1982); 79:1979-1983.
Wilson et al., "An Fcγ Receptor-Dependent Mechanism Drives Antibody-Mediated Target-Receptor Signaling in Cancer Cells," Cancer Cell (Jan. 2011); 19:101-113.
Li et al., "Inhibitory Fcγ Receptor Engagement Drives Adjuvant and Anti-Tumor Activities of Agonistic CD40 Antibodies," Science (Aug. 2011); 333::1030-1034.
White et al., "Interaction with FcγRIIB Is Critical for the Agonistic Activity of Anti-CD40 Monoclonal Antibody," Journal of Immunology (Aug. 2011); 187(4):1754-1763.
Mimoto et al., "Engineered antibody Fc variant with selectively enhanced FcγRIIb binding over both FcγRIIaR131 and FcγRIIaH131," Protein Engineering, Design & Selection (2013); 26(10):589-598.
Colman, "Effects of amino acid sequence changes on antibody-antigen interactions," Research in Immunology (1994); 145:33-36.
Kussie et al., "A Single Engineered Amino Acid Substitution Changes Antibody Fine Specificity," Journal of Immunology (1994); 152:146-152.
Chen et al., "Enhancement and destruction of antibody function by somatic mutation: unequal occurrence is controlled by V gene combinatorial associations," The EMBO Journal (1995); 14(12):2784-2794.
Jefferis, "Glycosylation as a strategy to improve antibody-based therapeutics," Nature Reviews / Drug Discovery (2009); 8:226-234.

(Continued)

*Primary Examiner* — Maher M Haddad
(74) *Attorney, Agent, or Firm* — Fox Rothschild LLP

(57) ABSTRACT

Provided herein are agonistic antibodies, or antigen binding portions thereof, that bind to human CD40. Such antibodies optionally comprise Fc regions with enhanced specificity for FcγRIIb. The invention also provides methods of treatment of cancer or chronic infection by administering the antibodies of the invention to a subject in need thereof.

4 Claims, 5 Drawing Sheets

Specification includes a Sequence Listing.

(56) References Cited

OTHER PUBLICATIONS

White et al., "Conformation of the Human Immunoglobulin G2 Hinge Imparts Superagonistic Properties to Immunostimulatory Anticancer Antibodies," Cancer Cell (2015); 27:138-148.

Vonderheide et al., "Agonistic CD40 antibodies and cancer therapy," Clin Cancer Res. (Mar. 1, 2013); 19(5):1035-1043.

Chu et al., "Inhibition of B cell receptor-mediated activation of primary human B cells by coengagement of CD19 and FcgRIIb with Fc-engineered antibodies", Molecular Immunology, 2008, 45, pp. 3926-3933.

Mimoto et al., "Crystal structure of a novel asymmetrically engineered Fc variant with improved affinity for FcgRs", Molecular Immunology, 2014, 58, pp. 132-138.

* cited by examiner

ANTIBODIES TO CD40 WITH ENHANCED AGONIST ACTIVITY

CROSS REFERENCE TO RELATED APPLICATIONS

This application is a Continuation of U.S. application Ser. No. 15/195,119, filed on Jun. 28, 2016, which claims priority to U.S. Provisional Application No. 62/304,012, filed Mar. 4, 2016. The contents of which are all incorporated herein by reference in their entireties.

BACKGROUND

Recent research has revealed that human cancers and chronic infections may be treated with agents that modulate the patient's immune response to malignant or infected cells. See, e.g., Reck & Paz-Ares (2015) *Semin. Oncol.* 42:402. Agonistic anti-CD40 antibodies, such as CP-870893 and dacetuzumab (SGN-40) have been tried for treating cancer based on the belief that they may enhance such an immune response. See, e.g., Kirkwood et al. (2012) *CA Cancer J. Clin.* 62:309; Vanderheide & Glennie (2013) *Clin. Cancer Res.* 19:1035. Recent experiments in mice have revealed that anti-CD40 antibodies with enhanced specificity for the inhibitory Fc receptor FcγRIIb have increased anti-tumor efficacy. See, e.g., WO 2012/087928; Smith, et al. (2012) *PNAS* 109(16):6181-6; Li & Ravetch (2012) *Proc. Nat'l Acad. Sci* (USA) 109:10966; Wilson et al. (2011) *Cancer Cell* 19:101; White et al. (2011) *J. Immunol.* 187:1754.

The need exists for improved agonistic anti-human CD40 antibodies for treatment of cancer and chronic infections in human subjects. Such antibodies will preferably have enhanced specificity for the inhibitory Fc receptor FcγRIIb as compared to activating Fc receptors, and will exhibit enhanced anti-tumor and/or anti-infective activity.

SUMMARY OF THE INVENTION

Provided herein are isolated monoclonal antibodies (e.g., murine monoclonal antibodies, humanized murine monoclonal antibodies, and human monoclonal antibodies) that specifically bind to human CD40 (the mature sequence of SEQ ID NO: 11), optionally having modified Fc regions that enhance specificity for binding to FcγRIIb receptor. Also provided are (i) antibodies that compete with the antibodies disclosed herein for binding to human CD40, and (ii) antibodies that bind to the same epitopes as the antibodies disclosed herein, i.e. antibodies that compete for binding to human CD40 with antibodies comprising a mutant Fc region having one or more mutations corresponding to one or more mutations in an IgG heavy chain selected from the group consisting of N297A, S267E ("SE"), S267E/L328F ("SELF"), G237D/P238D/P271G/A330R ("V9"), or G237D/P238D/H268D/P271G/A330R ("VII") (SEQ ID Nos: 3-7), such as antibodies that compete for binding to human CD40 with mAb 2141 IgG1, also termed CP-870,893.

In some embodiments the antibody of the present invention comprises a heavy chain and a light chain, wherein the heavy chain comprises CDRH1, CDRH2 and CDRH3 sequences and the light chain comprises CDRL1, CDRL2 and CDRL3 and Fc variants N297A, S267E ("SE"), S267E/L328F ("SELF"), G237D/P238D/P271G/A330R ("V9"), G237D/P238D/H268D/P271G/A330R ("V11"), as disclosed at Table 2.

In some embodiments, FC variants include a N297A (SEQ ID Nos: 2,3), SE (SEQ ID Nos: 2,4), SELF (SEQ ID Nos: 2,5), V9 (SEQ ID Nos: 2,6), and or V11 (SEQ ID Nos: 2,7). In alternative embodiments, anti-human CD40 antibodies of the present invention include antibodies comprising heavy and light chains consisting essentially of the sequences of these heavy and light chains, or comprise heavy and light chains sharing at least 80%, 85%, 90% and 95% sequence identity with these sequences. In some embodiments, the anti-huCD40 antibodies of the present invention comprise modified Fe regions with greater specificity for binding to FcγRIIb as opposed to binding to activating receptors than antibodies with naturally occurring Fc regions. In certain embodiments the A/I ratio for the anti-huCD40 antibody of the present invention is less than 5, and in preferred embodiments, less than 1.

In certain embodiments, the invention relates to anti-huCD40 antibodies or antigen binding fragments thereof that compete for binding with, cross-block, or bind to the same epitope as, one or more of antibodies comprising Fc variants N297A (SEQ ID Nos: 2,3), SE (SEQ ID Nos: 2,4), SELF (SEQ ID Nos: 2,5), V9 (SEQ ID Nos: 2,6), and or V11 (SEQ ID Nos: 2,7), including human or humanized antibodies.

In some embodiments the anti-huCD40 antibody of the present invention comprises one or more heavy chains and one or more light chains, such as two heavy chains and two light chains.

In some embodiments the isolated antibody, or antigen binding portion thereof, that
(i) specifically binds to human CD40; and
(ii) comprises a mutant Fc region having one or more mutations corresponding to one or more mutations in an IgG heavy chain selected from the group consisting of SEQ ID Nos: 3-7.

In some embodiments the isolated antibody or antigen binding portion thereof of competes for binding to human CD40 with CP-870,893 or ChiLob, 2141.

In some embodiments the antibody or antigen binding portion thereof of has an enhanced specificity of binding to FcγRIIb.

The present invention further provides nucleic acids encoding the heavy and/or light chain variable regions, of the anti-CD40 antibodies of the present invention, or antigen binding fragments thereof, expression vectors comprising the nucleic acid molecules, cells transformed with the expression vectors, and methods of producing the antibodies by expressing the antibodies from cells transformed with the expression vectors and recovering the antibody.

The present invention also provides pharmaceutical compositions comprising anti-huCD40 antibodies of the present invention, or antigen binding fragments thereof, and a pharmaceutically acceptable carrier.

The present invention provides a method of enhancing an immune response in a subject comprising administering an effective amount of an anti-huCD40 antibody of the present invention, or antigen binding fragment thereof, to the subject such that an immune response in the subject is enhanced. In certain embodiments, the subject has a tumor and an immune response against the tumor is enhanced. In another embodiment, the subject has a viral infection, e.g. a chronic viral infection, and an anti-viral immune response is enhanced.

The present invention also provides a method of inhibiting the growth of tumors in a subject comprising administering to the subject an anti-huCD40 antibody of the present invention, or antigen binding fragment thereof, such that growth of the tumor is inhibited.

The present invention further provides a method of treating cancer, e.g., by immunotherapy, comprising administering to a subject in need thereof a therapeutically effective amount an anti-huCD40 antibody of the present invention, or antigen binding fragment thereof, e.g. as a pharmaceutical composition, thereby treating the cancer. In certain embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In certain embodiments, the methods of modulating immune function and methods of treatment described herein comprise administering an anti-huCD40 antibody of the present invention in combination with, or as a bispecific reagent with, one or more additional therapeutics, for example, a second immunomodulatory antibody.

BRIEF DESCRIPTION OF THE DRAWINGS

FIG. 1A is a representative flow cytometry staining of mouse or human CD40 on the indicated splenic cell populations from CD40−/−huCD40+/+ and wild type mice. FIG. 1B is a representative flow cytometry staining of GC B cells from mesenteric LN of the indicated mouse type. Live B220+ cells were gated. GC B cells indicated as CD38-Fashi.

FIG. 1C illustrates an ELISA for detection of serum levels of influenza H1N1-specific IgG from mice immunized with recombinant influenza H1N1. Each dot represents individual mouse. FIG. 1D illustrates the binding specificity of the indicated Fc variants of anti-CD40 Ab clone 2141 assessed by ELISA using recombinant hCD40. Data are represented as means. See also Table 1.

FIG. 3A shows FcγRs binding profile of 2141 anti-CD40 Fc variants. See also Table 2.

FIG. 3B shows flow cytometry analysis for OVA-specific CD8+ T cells in the blood of humanized CD40/FcγR mice immunized with DEC-OVA in the presence or absence of the indicated CP-890,873 (left) or ChiLob 7/4 (right) anti-CD40 Fc variants. Each dot represents an individual mouse.

FIG. 4A indicates the fold-change in hFcγRIIB and hFcγRIIB/hFcγRIIA$^{R131}$ binding affinities of 2141 anti-CD40 Fc variants, based on SPR measurements. See also Table 2. FIG. 4B shows flow cytometry analysis for OVA-specific CD8+ T cells in the blood of huCD40/FcγR mice immunized with DEC-OVA in the presence or absence of the indicated CP-870,893 anti-CD40 Fc variants. Each dot represents an individual mouse. FIG. 4C shows platelet counts in blood 24 hours after administration of CP-870,893 anti-CD40 Fc variants into humanized CD40/FcγR mice. Each dot represents individual mouse. FIG. 4D shows hCD40$^+$/hFcγRIIA$^+$/hFcγRIIB$^+$ or hCD40$^+$/hFcγRIIA$^-$/hFcγRIIB$^+$ were immunized with DEC-OVA in the presence of CP-870,893-IgG2 and analyzed for the percentages of OVA-specific CD8+ T cells in the blood at day 7. See also Table 2.

FIG. 5A shows the change in total body weight over time after single injection of CP-870,893 Fc variant into humanized FcγR/CD40 mice. Data is represented as mean+/−SEM. n=4. FIG. 5B shows the platelet counts in humanized CD40/FcγR mice blood 7 days after administration of CP-870,893 anti-CD40 Fc variants. Each dot represents an individual mouse.

DETAILED DESCRIPTION

Figures 1A, 1B, 1C, 1D:
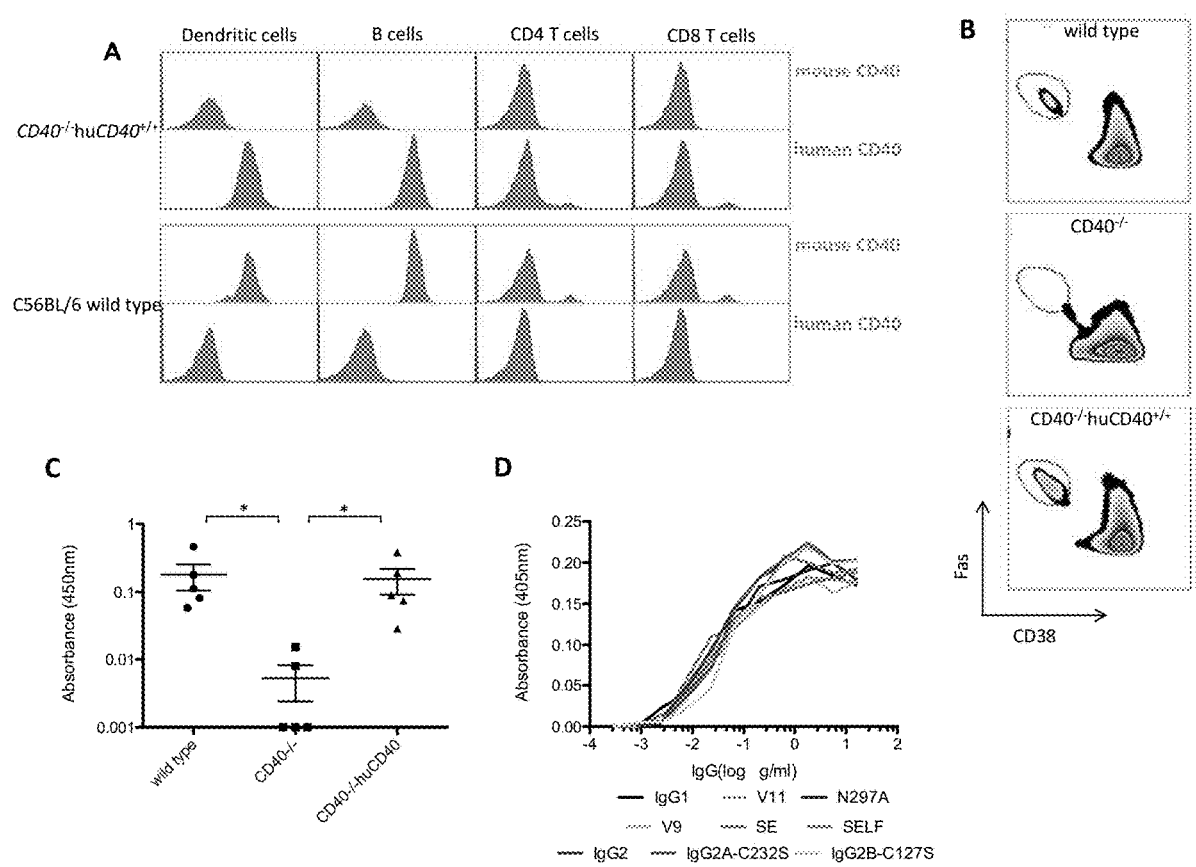
FIGS. 1A, 1B, 1C and 1D shows the characterization of CD40/FcγR humanized mice and 2141 anti-CD40 Fc variants.

The present invention provides isolated antibodies, particularly monoclonal antibodies, e.g., humanized or human monoclonal antibodies, that specifically bind to human CD40 ("huCD40") and have agonist activity. Sequences are provided for various humanized murine anti-huCD40 monoclonal antibodies. In certain embodiments, the antibodies described herein are derived from particular murine heavy and light chain germline sequences and/or comprise particular structural features such as CDR regions comprising particular amino acid sequences.

Further provided herein are methods of making such antibodies, immunoconjugates and bispecific molecules comprising such antibodies or antigen-binding fragments thereof, and pharmaceutical compositions formulated to contain the antibodies or fragments. Also provided herein are methods of using the antibodies for immune response enhancement, alone or in combination with other immunostimulatory agents (e.g., antibodies) and/or cancer or anti-infective therapies. Accordingly, the anti-huCD40 antibodies described herein may be used in a treatment in a wide variety of therapeutic applications, including, for example, inhibiting tumor growth and treating chronic viral infections.

Definitions

In order that the present description may be more readily understood, certain terms are first defined. Additional definitions are set forth throughout the detailed description.

CD40 refers to "TNF receptor superfamily member 5" (TNFRSF5). Unless otherwise indicated, or clear from the context, references to CD40 herein refer to human CD40 ("huCD40"), and anti-CD40 antibodies refer to anti-human CD40 antibodies. Human CD40 is further described at GENE ID NO: 958 and MIM (Mendelian Inheritance in Man): 109535. The sequence of human CD40 (NP_001241.1), including 20 amino acid signal sequence, is provided at SEQ ID NO: 11.

CD40 interacts with CD40 ligand (CD40L), which is also referred to as TNFSF5, gp39 and CD154. Unless otherwise indicated, or clear from the context, references to CD40L herein refer to human CD40L ("huCD40L"). Human CD40L is further described at GENE ID NO: 959 and MIM: 300386. The sequence of human CD40L (NP_000065.1) is provided at SEQ ID NO: 12.

Unless otherwise indicated or clear from the context, the term "antibody" as used to herein may include whole antibodies and any antigen-binding fragments (i.e., "antigen-binding portions") or single chains thereof. An "antibody" refers, in one embodiment, to a glycoprotein comprising at least two heavy (H) chains and two light (L) chains inter-connected by disulfide bonds, or an antigen binding fragment thereof. Each heavy chain is comprised of a heavy chain variable region (abbreviated herein as $V_H$) and a heavy chain constant region. In certain naturally occurring IgG, IgD and IgA antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four framework regions (FRs), arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human CD40 might also cross-react with CD40 from certain non-human primate species (e.g., cynomolgus monkey), but might not cross-react with CD40 from other species, or with an antigen other than CD40.

Unless otherwise indicated, an immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., human IgG1, exist in several allotypes, which differ from each other in at most a few amino acids. Unless otherwise indicated, "antibody" may include, by way of example, monoclonal and polyclonal antibodies; chimeric and humanized antibodies; human and non-human antibodies; wholly synthetic antibodies; and single chain antibodies.

The term "antigen-binding portion" or "antigen binding fragment" of an antibody, as used herein, refers to one or more fragments of an antibody that retain the ability to specifically bind to an antigen (e.g., human CD40). Examples of binding fragments encompassed within the term "antigen-binding portion/fragment" of an antibody include (i) a Fab fragment—a monovalent fragment consisting of the $V_L$, $V_H$, $C_L$ and CH1 domains; (ii) a F(ab')2 fragment—a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, and (v) a dAb fragment (Ward et al. (1989) Nature 341:544-546) consisting of a $V_H$ domain. An isolated complementarity determining region (CDR), or a combination of two or more isolated CDRs joined by a synthetic linker, may comprise and antigen binding domain of an antibody if able to bind antigen.

Single chain antibody constructs are also included in the invention. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv); see e.g., Bird et al. (1988) Science 242:423-426; and Huston et al. (1988) Proc. Natl. Acad. Sci. (USA) 85:5879-5883). Such single chain antibodies are also intended to be encompassed within the term "antigen-binding portion/fragment" of an antibody. These and other potential constructs are described at Chan & Carter (2010) Nat. Rev. Immunol. 10:301. These antibody fragments are obtained using conventional techniques known to those with skill in the art, and the fragments are screened for utility in the same manner as are intact antibodies. Antigen-binding portions/fragments can be produced by recombinant DNA techniques, or by enzymatic or chemical cleavage of intact immunoglobulins.

Unless otherwise indicated, the word "fragment" when used with reference to an antibody, such as in a claim, refers to an antigen binding fragment of the antibody, such that "antibody or fragment" has the same meaning as "antibody or antigen binding fragment thereof."

A "bispecific" or "bifunctional antibody" is an artificial hybrid antibody having two different heavy/light chain pairs, giving rise to two antigen binding sites with specificity for different antigens. Bispecific antibodies can be produced by a variety of methods including fusion of hybridomas or linking of Fab' fragments. See, e.g., Songsivilai & Lachmann (1990) Clin. Exp. Immunol. 79:315-321; Kostelny et al. (1992) J. Immunol. 148, 1547-1553.

The term "monoclonal antibody," as used herein, refers to an antibody that displays a single binding specificity and affinity for a particular epitope or a composition of antibodies in which all antibodies display a single binding specificity and affinity for a particular epitope. Typically such monoclonal antibodies will be derived from a single cell or nucleic acid encoding the antibody, and will be propagated without intentionally introducing any sequence alterations. Accordingly, the term "human monoclonal antibody" refers to a monoclonal antibody that has variable and optional constant regions derived from human germline immunoglobulin sequences. In one embodiment, human monoclonal antibodies are produced by a hybridoma, for example, obtained by fusing a B cell obtained from a transgenic or transchromosomal non-human animal (e.g., a transgenic mouse having a genome comprising a human heavy chain transgene and a light chain transgene), to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations that occur, for example, during antibody maturation. As known in the art (see, e.g., Lonberg (2005) *Nature Biotech.* 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid sequences that encode the light chain and heavy chain immunoglobulin polypeptides in response to an antigen may not be identical to the original germline sequences, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. Human antibodies of the present invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to an antibody in which some, most or all of the amino acids outside the CDR domains of a non-human antibody, e.g. a mouse antibody, are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody. A "hybrid" antibody refers to an antibody having heavy and light chains of different types, such as a mouse (parental) heavy chain and a humanized light chain, or vice versa.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in one or a few amino acids. See, e.g., Jefferis et al. (2009) *mAbs* 1:1.

The phrases "an antibody recognizing an antigen" and "an antibody specific for an antigen" are used interchangeably herein with the term "an antibody that binds specifically to an antigen."

An "isolated antibody," as used herein, refers to an antibody that is substantially free of other antibodies having different antigenic specificities (e.g., an isolated antibody that specifically binds to CD40 is substantially free of antibodies that specifically bind antigens other than CD40). An isolated antibody that specifically binds to an epitope of CD40 may, however, have cross-reactivity to other CD40 proteins from different species.

"Effector functions," deriving from the interaction of an antibody Fc region with certain Fc receptors, include but are not necessarily limited to C1q binding, complement dependent cytotoxicity (CDC), Fc receptor binding, FcγR-mediated effector functions such as ADCC and antibody dependent cell-mediated phagocytosis (ADCP), and down regulation of a cell surface receptor (e.g., the B cell receptor; BCR). Such effector functions generally require the Fc region to be combined with an antigen binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIb, or equivalently FcγRIIB) receptor. Various properties of human FcγRs are summarized in Table 1. The majority of innate effector cell types co-express one or more activating FcγR and the inhibitory FcγRIIb, whereas natural killer (NK) cells selectively express one activating Fc receptor (FcγRIII in mice and FcγRIIIA in humans) but not the inhibitory FcγRIIb in mice and humans. Human IgG1 binds to most human Fc receptors and is considered equivalent to murine IgG2a with respect to the types of activating Fc receptors that it binds to.

TABLE 1

Properties of Human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dendritic cells? |
| FcγRIIA | H131 | Low to medium | IgG1 > 3 > 2 > 4 | Neutrophils, monocytes, macrophages, |
|  | R131 | Low | IgG1 > 3 > 4 > 2 | eosinophils, dendritic cells, platelets |
| FcγRIIIA | V158 | Medium | IgG1 = 3 >> 4 > 2 | NK cells, monocytes, macrophages, mast |
|  | F158 | Low | IgG1 = 3 >> 4 > 2 | cells, eosinophils, dendritic cells? |

TABLE 1-continued

Properties of Human FcγRs

| Fcγ | Allelic variants | Affinity for human IgG | Isotype preference | Cellular distribution |
|---|---|---|---|---|
| FcγRIIb | I232 | Low | IgG1 = 3 = 4 > 2 | B cells, monocytes, macrophages, dendritic |
| | T232 | Low | IgG1 = 3 = 4 > 2 | cells, mast cells |

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fe region comprises the constant region of an antibody excluding the first constant region immunoglobulin domain (e.g., CH1 or CL). In IgG, IgA and IgD antibody isotypes, the Fc region comprises CH2 and CH3 constant domains in each of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 (e.g., SEQ ID NO: 14) or P230 (e.g., SEQ ID NO: 15) (or an amino acid between these two amino acids) to the carboxy-terminus of the heavy chain, wherein the numbering is according to the EU index as in Kabat. Kabat et al. (1991) Sequences of Proteins of Immunological Interest, National Institutes of Health, Bethesda, MD; see also FIGS. 3c-3f of U.S. Pat. App. Pub. No. 2008/0248028. The CH2 domain of a human IgG Fc region extends from about amino acid 231 to about amino acid 340, whereas the CH3 domain is positioned on C-terminal side of a CH2 domain in an Fc region, i.e., it extends from about amino acid 341 to about amino acid 447 of an IgG (including a C-terminal lysine). As used herein, the Fc region may be a native sequence Fc, including any allotypic variant, or a variant Fe (e.g., a non-naturally occurring Fe). Fc may also refer to this region in isolation or in the context of an Fe-comprising protein polypeptide such as a "binding protein comprising an Fc region," also referred to as an "Fe fusion protein" (e.g., an antibody or immunoadhesin).

A "native sequence Fc region" or "native sequence Fc" comprises an amino acid sequence that is identical to the amino acid sequence of an Fc region found in nature. Native sequence human Fe regions include a native sequence human IgG1 Fc region; native sequence human IgG2 Fc region; native sequence human IgG3 Fe region; and native sequence human IgG4 Fe region as well as naturally occurring variants thereof. Native sequence Fc includes the various allotypes of Fes. See, e.g., Jefferis et al. (2009) mAbs 1:1.

The term "epitope" or "antigenic determinant" refers to a site on an antigen (e.g., huCD40) to which an immunoglobulin or antibody specifically binds. Epitopes within protein antigens can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation.

The term "epitope mapping" refers to the process of identification of the molecular determinants on the antigen involved in antibody-antigen recognition. Methods for determining what epitopes are bound by a given antibody are well known in the art and include, for example, immunoblotting and immunoprecipitation assays, wherein overlapping or contiguous peptides from (e.g., from CD40) are tested for reactivity with a given antibody (e.g., anti-CD40 antibody); x-ray crystallography; 2-dimensional nuclear magnetic resonance; yeast display; and HDX-MS (see, e.g., Epitope Mapping Protocols in Methods in Molecular Biology, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on CD40" with the antibodies described herein include, for example, epitope mapping methods, such as, x-ray analyses of crystals of antigen: antibody complexes, which provide atomic resolution of the epitope, and hydrogen/deuterium exchange mass spectrometry (HDX-MS). Other methods monitor the binding of the antibody to antigen fragments (e.g. proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) Science 244:1081) or yeast display of mutant target sequence variants. In addition, computational combinatorial methods for epitope mapping can also be used. These methods rely on the ability of the antibody of interest to affinity isolate specific short peptides from combinatorial phage display peptide libraries. Antibodies having the same or closely related $V_L$ and $V_H$ or the same CDR sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb. Protoc.; 2006; doi:10.1101/pdb.prot4277 or in Chapter 11 of "Using Antibodies" by Ed Harlow and David Lane, Cold Spring Harbor Laboratory Press, Cold Spring Harbor, NY, USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al. (1983) Methods in Enzymology 9:242); solid phase direct biotin-avidin EIA (see Kirkland et al. (1986) *J. Immunol.* 137:3614); solid phase direct labeled assay, solid phase direct labeled sandwich assay (see Harlow and Lane (1988), Antibodies: A Laboratory Manual, Cold Spring Harbor Press); solid phase direct label RIA using I-125 label (see Morel et al. (1988) *Mol. Immunol.* 25(1):7); solid phase direct biotin-avidin EIA (Cheung et al. (1990) *Virology* 176:546); and direct labeled RIA. (Moldenhauer et al. (1990) *Scand. J. Immunol.* 32:77).

As used herein, the terms "specific binding," "selective binding," "selectively binds," and "specifically binds," refer to antibody binding to an epitope on a predetermined antigen but not to other antigens. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 surface plasmon resonance instrument using the predetermined antigen, e.g., recombinant human CD40, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human CD40" refers to an antibody that binds to soluble or cell bound human CD40 with a $K_D$ of $10^{-7}$ M or less, such as approximately less than $10^{-8}$ M, $10^{-9}$ M or $10^{-10}$ M or even lower. An antibody that "cross-reacts with cynomolgus CD40" refers to an antibody that binds to cynomolgus CD40 with a $K_D$ of $10^{-7}$M or less, such as approximately less than $10^{-8}$ M, $10^{-9}$ M or $10^{-10}$ M or even lower.

The term "$k_{assoc}$" or "$K_A$," as used herein, refers to the association rate constant of a particular antibody-antigen interaction, whereas the term "$k_{dis}$" or "$K_D$," as used herein, refers to the dissociation rate constant of a particular antibody-antigen interaction. The term "$K_D$", as used herein, refers to the equilibrium dissociation constant, which is obtained from the ratio of $K_D$ to $K_A$ (i.e., $K_D/K_A$) and is expressed as a molar concentration (M). $K_D$ values for antibodies can be determined using methods well established in the art. A preferred method for determining the $K_D$ of an antibody is biolayer interferometry (BLI) analysis, preferably using a ForteBio Octet RED device, surface plasmon resonance, preferably using a biosensor system such as a BIACORE surface plasmon resonance system (see Example 5), or flow cytometry and Scatchard analysis.

The term "EC50" in the context of an in vitro or in vivo assay using an antibody or antigen binding fragment thereof, refers to the concentration of an antibody or an antigen-binding fragment thereof that induces a response that is 50% of the maximal response, i.e., halfway between the maximal response and the baseline.

The term "binds to immobilized CD40" refers to the ability of an antibody described herein to bind to CD40, for example, expressed on the surface of a cell or attached to a solid support.

The term "cross-reacts," as used herein, refers to the ability of an antibody described herein to bind to CD40 from a different species. For example, an antibody described herein that binds human CD40 may also bind CD40 from another species (e.g., cynomolgus CD40). As used herein, cross-reactivity may be measured by detecting a specific reactivity with purified antigen in binding assays (e.g., SPR, ELISA) or binding to, or otherwise functionally interacting with, cells physiologically expressing CD40. Methods for determining cross-reactivity include standard binding assays as described herein, for example, by BIACORE surface plasmon resonance (SPR) analysis using a BIACORE 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" to the antibody sequence provided herein, i.e. nucleotide and amino acid sequence modifications that do not abrogate the binding of the antibody encoded by the nucleotide sequence or containing the amino acid sequence, to the antigen. For example, modifications can be introduced by standard techniques known in the art, such as site-directed mutagenesis and PCR-mediated mutagenesis. Conservative sequence modifications include conservative amino acid substitutions, in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-CD40 antibody is preferably replaced with another amino acid residue from the same side chain family. Methods of identifying nucleotide and amino acid conservative substitutions that do not eliminate antigen binding are well-known in the art. See, e.g., Brummell et al. (1993) *Biochem.* 32:1180-1187; Kobayashi et al. (1999) *Protein Eng.* 12(10):879-884; and Burks et al. (1997) *Proc. Natl. Acad. Sci.* (USA) 94:412-417.

Alternatively, in another embodiment, mutations can be introduced randomly along all or part of an anti-CD40 antibody coding sequence, such as by saturation mutagenesis, and the resulting modified anti-CD40 antibodies can be screened for improved binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences when the sequences are optimally aligned (i.e., % homology=# of identical positions/total # of positions×100), with optimal alignment determined taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna. CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch ((1970) *J. Mol. Biol.* (48):444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition or depletion of a $T_{reg}$ cell. "T effector" ("$T_{eff}$") cells refers to T cells (e.g., CD4+ and CD8+ T cells) with cytolytic activities as well as T helper (Th) cells, which secrete cytokines and activate and direct other immune cells, but does not include regulatory T cells ($T_{reg}$ cells).

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

An "immunomodulator" or "immunoregulator" refers to an agent, e.g., a component of a signaling pathway that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "linked" refers to the association of two or more molecules. The linkage can be covalent or non-covalent. The linkage also can be genetic (e.g., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the terms "inhibits" or "blocks" are used interchangeably and encompass both partial and complete inhibition/blocking by at least about 50%, for example, at least about 60%, 70%, 80%, 90%, 95%, 99%, or 100%.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Prophylaxis refers to administration to a subject who does not have a disease, to prevent the disease from occurring or minimize its effects if it does.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, inhibits the development or recurrence of the disease. The ability of a therapeutic or prophylactic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that slows cancer progression or promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. Pharmacological effectiveness refers to the ability of the drug to promote cancer regression in the patient. Physiological safety refers to an acceptably low level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Inhibition of tumor growth may not be immediate after treatment, and may only occur after a period of time or after repeated administration. Alternatively, this property of a composition can be evaluated by examining the ability of the compound to inhibit cell growth, such inhibition can be measured in vitro by assays known to the skilled practitioner. In other preferred embodiments described herein, tumor regression may be observed and may continue for a period of at least about 20 days, more preferably at least about 40 days, or even more preferably at least about 60 days.

"Combination" therapy, as used herein, unless otherwise clear from the context, is meant to encompass administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. See, e.g., Kohrt et al. (2011) *Blood* 117:2423.

The terms "patient" and "subject" refer to any human that receives either prophylactic or therapeutic treatment. For example, the methods and compositions described herein can be used to treat a subject having cancer.

Various aspects described herein are described in further detail in the following subsections.

I. Anti-CD40 Antibodies

The present application discloses agonistic anti-huCD40 antibodies having desirable properties for use as therapeutic agents in treating diseases such as cancers. These properties include one or more of the ability to bind to human CD40 with high affinity, acceptably low immunogenicity in human subjects, the ability to bind preferentially to FcγRIIb, and the absence of sequence liabilities that might reduce the chemical stability of the antibody.

The anti-CD40 antibodies disclosed herein by sequence bind to specific epitopes on human CD40. Other antibodies that bind to the same or closely related epitopes would likely share these desirable properties, and may be discovered doing competition experiments.

Anti-huCD40 Antibodies that Compete with Anti-huCD40 Antibodies Disclosed Herein Anti-huCD40 antibodies that compete with the antibodies of the present invention for binding to huCD40 may be raised using immunization protocols similar to those described herein (Examples 1 and 2). Antibodies that compete for binding with the anti-huCD40 antibodies disclosed herein by sequence may also be generated by immunizing mice or other non-human animal with human CD40 or a construct comprising the extracellular domain thereof (residues 21-193 of SEQ ID NO: 11), or by immunizing with a fragment of human CD40 containing the epitope bound by the anti-huCD40 antibodies disclosed herein. The resulting antibodies can be screened for the ability to block binding of an antibody comprising a mutant Fc region having one or more mutations corresponding to one or more mutations in an IgG heavy chain selected from the group consisting of N297A, SE, SELF, V9, and or V 11 (SEQ ID Nos: 3-7), to human CD40 by methods well known in the art, for example blocking binding to fusion protein of the extracellular domain of CD40 and an immunoglobulin Fc domain in a ELISA, or blocking the ability to bind to cells expressing huCD40 on their surface, e.g. by FACS. In various embodiments, the test antibody is contacted with the CD40-Fc fusion protein (or to cells expressing huCD40 on their surface) prior to, at the same time as, or after the addition of an antibody comprising a mutant Fc region having one or more mutations corresponding to one or more mutations in an IgG heavy chain selected from the group consisting of N297A, SE, SELF, V9, and or V11 (SEQ ID Nos: 3-7). For example, "binning" experiments may be performed to determine whether a test antibody falls into the same "bin" as an antibodies disclosed herein by sequence, with antibodies disclosed herein by sequence as the "reference" antibodies and the antibodies to be tested as the "test" antibodies. Antibodies that reduce binding of the antibodies disclosed herein by sequence to human CD40 (either as an Fc fusion or on a cell), particularly at roughly stoichiometric concentrations, are likely to bind at the same, overlapping, or adjacent epitopes, and thus may share the desirable functional properties of an antibody comprising a mutant Fc region having one or more mutations corresponding to one or more mutations in an IgG heavy chain selected from the group consisting of N297A, SE, SELF, V9, and or V11 (SEQ ID Nos: 3-7).

Accordingly, provided herein are anti-huCD40 antibodies that inhibit the binding of an anti-huCD40 antibodies described herein to huCD40 on cells by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or by 100%, and/or whose binding to huCD40 on cells is inhibited by an anti-huCD40 antibodies described herein by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or by 100%, e.g., as measured by ELISA or FACS, such as by using the assay described in the following paragraph.

An exemplary competition experiment to determine whether a test antibody blocks the binding of (i.e., "competes with") a reference antibody, may be conducted as follows: cells expressing CD40 are seeded at 105 cells per sample well in a 96 well plate. The plate is set on ice followed by the addition of unconjugated test antibody at concentrations ranging from 0 to 50 μg/mL (three-fold titration starting from a highest concentration of 50 μg/mL). An unrelated IgG may be used as an isotype control for the first antibody and added at the same concentrations (three-fold titration starting from a highest concentration of 50 μg/mL). A sample pre-incubated with 50 μg/mL unlabeled reference antibody may be included as a positive control for complete blocking (100% inhibition) and a sample without antibody in the primary incubation may be used as a negative control (no competition; 0% inhibition). After 30 minutes of incubation, labeled, e.g., biotinylated, reference antibody is added at a concentration of 2 μg/mL per well without washing. Samples are incubated for another 30 minutes on ice. Unbound antibodies are removed by washing the cells with FACS buffer. Cell-bound labeled reference antibody is detected with an agent that detects the label, e.g., PE conjugated streptavidin (Invitrogen, catalog #S21388) for detecting biotin. The samples are acquired on a FACS Calibur Flow Cytometer (BD, San Jose) and analyzed with FLOWJO software (Tree Star, Inc, Ashland, OR). The results may be represented as the % inhibition (i.e., subtracting from 100% the amount of label at each concentration divided by the amount of label obtained with no blocking antibody).

Typically, the same experiment is then conducted in the reverse, i.e., the test antibody is the reference antibody and the reference antibody is the test antibody. In certain embodiments, an antibody at least partially (e.g., at least 10%, 20%, 30%, 40%, 50%, 60%, 70%, 80%, or 90%) or completely (100%) blocks the binding of the other antibody to the target, e.g. human CD40 or fragment thereof, and regardless of whether inhibition occurs when one or the other antibody is the reference antibody. A reference antibody and a test antibody "cross-block" binding of each other to the target when the antibodies compete with each other both ways, i.e., in competition experiments in which the reference antibody is added first and in competition experiments in which the test antibody is added first.

Anti-huCD40 Antibodies that Bind to the Same Epitope

Anti-huCD40 antibodies that bind to the same or similar epitopes to the antibodies disclosed herein may be raised using immunization protocols similar to those described herein. The resulting antibodies can be screened for high affinity binding to human CD40. Selected antibodies can then be studied in yeast display assay in which sequence variants of huCD40 are presented on the surface of yeast cells, or by hydrogen-deuterium exchange experiments, to determine the precise epitope bound by the antibody.

Epitope determinations may be made by any method known in the art. In various embodiments, anti-huCD40 antibodies are considered to bind to the same epitope as an anti-huCD40 mAb disclosed herein if they make contact with one or more of the same residues within at least one region of huCD40; if they make contacts with a majority of the residues within at least one region of huCD40; if they make contacts with a majority of the residues within each region of huCD40; if they make contact with a majority of contacts along the entire length of huCD40; if they make contacts within all of the same distinct regions of human CD40; if they make contact with all of the residues at any one region on human CD40; or if they make contact with all of the same residues at all of the same regions. Epitope "regions" are clusters of residues along the primary sequence.

Techniques for determining antibodies that bind to the "same epitope on huCD40" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to a modification of an amino acid residue within the antigen sequence is often considered an indication of an epitope component. Methods may also rely on the ability of an antibody of interest to affinity isolate specific short peptides (either in native three dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning CD40. Alternatively, the method of Jespers et al. (1994) *Biotechnology* 12:899 may be used to guide the selection of antibodies having the same epitope and therefore similar properties to the an anti-CD40 antibodies described herein. Using phage display, first the heavy chain of the anti-CD40 antibody is paired with a repertoire of (preferably human) light chains to select a CD40-binding antibody, and then the new light chain is paired with a repertoire of (preferably human) heavy chains to select a (preferably human) CD40-binding antibody having the same epitope or epitope region as an anti-huCD40 antibody described herein. Alternatively variants of an antibody described herein can be obtained by mutagenesis of cDNA encoding the heavy and light chains of the antibody.

Alanine scanning mutagenesis, as described by Cunningham & Wells (1989) *Science* 244: 1081, or some other form of point mutagenesis of amino acid residues in CD40 (such as the yeast display method provided at Example 6) may also be used to determine the functional epitope for an anti-CD40 antibody.

The epitope or epitope region (an "epitope region" is a region comprising the epitope or overlapping with the epitope) bound by a specific antibody may also be determined by assessing binding of the antibody to peptides comprising fragments of CD40. A series of overlapping peptides encompassing the sequence of CD40 (e.g., human CD40) may be synthesized and screened for binding, e.g. in a direct ELISA, a competitive ELISA (where the peptide is assessed for its ability to prevent binding of an antibody to CD40 bound to a well of a microtiter plate), or on a chip. Such peptide screening methods may not be capable of detecting some discontinuous functional epitopes, i.e. functional epitopes that involve amino acid residues that are not contiguous along the primary sequence of the CD40 polypeptide chain.

An epitope may also be identified by MS-based protein footprinting, such as hydrogen/deuterium exchange mass spectrometry (HDX-MS) and Fast Photochemical Oxidation of Proteins (FPOP). HDX-MS may be conducted, e.g., as further described at Wei et al. (2014) *Drug Discovery Today* 19:95, the methods of which are specifically incorporated by reference herein. FPOP may be conducted as described, e.g., in Hambley & Gross (2005) *J. American Soc. Mass Spectrometry* 16:2057, the methods of which are specifically incorporated by reference herein.

The epitope bound by anti-CD40 antibodies may also be determined by structural methods, such as X-ray crystal structure determination (e.g., WO 2005/044853), molecular modeling and nuclear magnetic resonance (NMR) spectroscopy, including NMR determination of the H-D exchange rates of labile amide hydrogens in CD40 when free and when bound in a complex with an antibody of interest (Zinn-Justin et al. (1992) *Biochemistry* 31:11335; Zinn-Justin et al. (1993) *Biochemistry* 32:6884).

With regard to X-ray crystallography, crystallization may be accomplished using any of the known methods in the art (e.g. Giege et al. (1994) *Acta Crystallogr. D* 50:339; McPherson (1990) *Eur. J. Biochem.* 189:1), including microbatch (e.g. Chayen (1997) *Structure* 5:1269), hanging-drop vapor diffusion (e.g. McPherson (1976) *J. Biol. Chem.* 251:6300), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) *Meth. Enzymol.* 114 & 115, H. W. Wyckoff et al., eds., Academic Press; U.S. Patent Application Publication No. 2004/0014194), and BUSTER (Bricogne (1993) Acta Cryst. D 49:37-60; Bricogne (1997) *Meth. Enzymol.* 276A:361-423, Carter & Sweet, eds.; Roversi et al. (2000) *Acta Cryst. D* 56:1313-1323), the disclosures of which are hereby incorporated by reference in their entireties.

Unless otherwise indicated, and with reference to the claims, the epitope bound by an antibody is the epitope as determined by HDX-MS methods.

Anti-CD40 Antibodies that Bind with High Affinity

In some embodiments the anti-huCD40 antibodies of the present invention bind to huCD40 with high affinity, like the anti-huCD40 antibodies disclosed herein, increasing their likelihood of being effective therapeutic agents. In various embodiments anti-huCD40 antibodies of the present invention bind to huCD40 with a $K_D$ of less than 10 nM, 5 nM, 2 nM, 1 nM, 300 pM or 100 pM. In other embodiments, the anti-huCD40 antibodies of the present invention bind to huCD40 with a $K_D$ between 2 nM and 100 pM. Standard assays to evaluate the binding ability of the antibodies toward huCD40 include ELISAs, RIAs, Western blots, biolayer interferometry (BLI) and BIACORE SPR analysis.

Anti-CD40 Antibody Sequence Variants

Some variability in the antibody sequences disclosed herein may be tolerated and still maintain the desirable properties of the antibody. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Accordingly, the present invention further provides anti-huCD40 antibodies comprising CDR sequences that are at least 70%, 75%, 80%, 85%, 90%, 95%, 96%, 97%, 98%, or 99% identical to the CDR sequences of the antibodies disclosed herein. The present invention also provides anti-huCD40 antibodies comprising heavy and/or light chain variable domain sequences that are at least 70%, 75%, 80%, 85%, 90%, 95%, 96%, 97%, 98%, or 99% identical to the heavy and/or light chain variable domain sequences of an antibody comprising a mutant Fc region having one or more mutations corresponding to one or more mutations in an IgG heavey chain selected from the group consisting of N297A, SE, SELF, V9, and or V 11 (SEQ ID Nos: 3-7), and humanized derivatives thereof).

As used herein, a murine antibody comprises heavy or light chain variable regions that are "derived from" a particular germline sequence if the variable regions of the antibody are obtained from a system that uses murine germline immunoglobulin genes, and the antibody sequence is sufficiently related to the germline that it is more likely derived from the given germline than from any other. Such systems include immunizing a mouse with the antigen of interest. The murine germline immunoglobulin sequence(s) from which the sequence of an antibody is "derived" can be identified by comparing the amino acid sequence of the antibody to the amino acid sequences of murine germline immunoglobulins and selecting the germline immunoglobulin sequence that is closest in sequence (i.e., greatest % identity) to the sequence of the antibody. A murine antibody that is "derived from" a particular germline immunoglobulin sequence may contain amino acid differences as compared to the germline sequence due to, for example, naturally-occurring somatic mutations or intentional introduction of site-directed mutation. However, a selected murine antibody typically is at least 90% identical in amino acids sequence to an amino acid sequence encoded by a germline immunoglobulin gene (e.g. V regions). In certain cases, a murine antibody may be at least 95%, or even at least 96%, 97%, 98%, or 99% identical in amino acid sequence to the amino acid sequence encoded by the germline immunoglobulin gene (e.g. V regions). Typically, an antibody derived from a particular murine germline sequence will display no more than 10 amino acid differences from the amino acid sequence encoded by the germline immunoglobulin gene (e.g. V regions). In certain cases, the murine antibody may comprise no more than 5, or even no more than 4, 3, 2, or 1 amino acid difference from the amino acid sequence encoded by the germline immunoglobulin gene (e.g. V regions).

II. Engineered and Modified Antibodies $V_H$ and $V_L$ Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Such grafting is of particular use in humanizing non-human anti-CD40 antibodies that compete for binding with the anti-huCD40 antibodies disclosed herein and/or bind to the same epitope as the anti-huCD40 antibodies disclosed herein. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific reference antibodies by constructing expression vectors that include CDR sequences from the specific reference antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See.* (USA) 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline V$_H$ Sequences Reveals about Fifty Groups of V$_H$ Segments with Different Hypervariable Loops" *J. Mol. Biol.* 227:776-798; and Cox, J. P. L. et al. (1994) "A Directory of Human Germ-line V$_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The V$_H$ CDR1, 2 and 3 sequences, and the V$_L$ CDR1, 2 and 3 sequences, can be grafted onto framework regions that have the identical sequence as that found in the germline immunoglobulin gene from which the framework sequence derive, or the CDR sequences can be grafted onto framework regions that contain up to 20, preferably conservative, amino acid substitutions as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Engineered antibodies described herein include those in which modifications have been made to framework residues within V$_H$ and/or V$_L$, e.g. to improve the properties of the antibody. Often such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest. Preferably conservative modifications are introduced. The mutations may be amino acid additions, deletions, or preferably substitutions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-CD40 antibodies that have one or more methionine residues in the heavy and/or light chain CDRs replaced with amino acid residues that do not undergo oxidative degradation. Similarly, deamidation sites may be removed from anti-CD40 antibodies, particularly in the CDRs. Potential glycosylation sites within the antigen binding domain are preferably eliminated to prevent glycosylation that may interfere with antigen binding. See, e.g., U.S. Pat. No. 5,714,350.

Fcs and Modified Fcs

Antibodies of the present invention may comprise the variable domains of the invention combined with constant domains comprising different Fc regions, selected based on the biological activities (if any) of the antibody for the intended use. Salfeld (2007) *Nat. Biotechnol.* 25:1369. Human IgGs, for example, can be classified into four subclasses, IgG1, IgG2, IgG3, and IgG4, and each these of these comprises an Fc region having a unique profile for binding to one or more of Fcγ receptors (activating receptors FcγRI (CD64), FcγRIIA, FcγRIIC (CD32a,c); FcγRIIIA and FcγRIIIB (CD16a,b) and inhibiting receptor FcγRIIB (CD32b), and for the first component of complement (C1q). Human IgG1 and IgG3 bind to all Fcγ receptors; IgG2 binds to FcγRIIAH131, and with lower affinity to FcγRIIAR131 FcγRIIIAV158; IgG4 binds to FcγRI, FcγRIIA, FcγRIIB, FcγRIIC, and FcγRIIIAV158; and the inhibitory receptor FcγRIIB has a lower affinity for IgG1, IgG2 and IgG3 than all other Fcγ receptors. Bruhns et al. (2009) *Blood* 113:3716. Studies have shown that FcγRI does not bind to IgG2, and FcγRIIIB does not bind to IgG2 or IgG4. Id. In general, with regard to ADCC activity, human IgG1≥IgG3>>IgG4≥IgG2. As a consequence, for example, an IgG1 constant domain, rather than an IgG2 or IgG4, might be chosen for use in a drug where ADCC is desired; IgG3 might be chosen if activation of FcγRIIIA-expressing NK cells, monocytes of macrophages; and IgG4 might be chosen if the antibody is to be used to desensitize allergy patients. IgG4 may also be selected if it is desired that the antibody lack all effector function.

Anti-huCD40 variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16 (t), G3m6(c3), G3m24(c5), G3m26(u), G3m27(v). See, e.g., Jefferis et al. (2009) mAbs 1:1). Selection of allotype may be influenced by the potential immunogenicity concerns, e.g. to minimize the formation of anti-drug antibodies.

In preferred embodiments, anti-CD40 antibodies of the present invention have an Fc that binds to or has enhanced binding to FcγRIIb, which can provide enhanced agonism. See, e.g., WO 2012/087928; Li & Ravetch (2011) *Science* 333:1030; Wilson et al. (2011) *Cancer Cell* 19:101; White et al. (2011) *J. Immunol.* 187:1754. Variable regions described herein may be linked to Fc variants that enhance affinity for the inhibitory receptor FcγRIIb, e.g. to enhance apoptosis-inducing or adjuvant activity. Li & Ravetch (2012) *Proc. Nat'l Acad. Sci.* (USA) 109:10966; U.S. Patent Application Publication No. 2014/0010812. Such variants may provide an antibody with immunomodulatory activities related to FcγRIIb+ cells, including for example B cells and monocytes. In one embodiment, the Fc variants provide selectively enhanced affinity to FcγRIIb relative to one or more activating receptors. Such variants may also exhibit enhanced FcR-mediated cross-linking, resulting in enhanced therapeutic efficacy. Modifications for altering binding to FcγRIIb include one or more modifications at a position selected from the group consisting of 234, 235, 236, 237, 239, 266, 267, 268, 325, 326, 327, 328, and 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y-267E, 236D-267E, 239D-268D, 239D-267E, 267E-268D, 267E-268E, and 267E-328F. Specifically, the S267E, G236D, S239D, L328F and I332E variants, including the S267E-L328F double variant, of human IgG1 are of particular value in specifically enhancing affinity for the inhibitory FcγRIIb receptor. Chu et al. (2008) *Mol. Immunol.* 45:3926; U.S. Patent Application Publication No. 2006/024298; WO 2012/087928. Enhanced specificity for FcγRIIb (as distinguished from FcγRIIa$_{R131}$) may be obtained by adding the P238D substitution and other mutations (Mimoto et al. (2013) *Protein. Eng. Des. & Selection* 26:589; WO 2012/1152410), as well as V262E and V264E (Yu et al. (2013) *J. Am. Chem. Soc.* 135:9723, and WO 2014/184545. See Table 2.

Half-Life Extension

In certain embodiments, the antibody is modified to increase its biological half-life. Various approaches are possible. For example, this may be done by increasing the binding affinity of the Fc region for FcRn. In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., (2004), *J. Biol. Chem.* 279(8): 6213-6216, Hinton et al. (2006) *Journal of Immunology* 176:346-356), 256A, 272A, 305A, 307A, 311A, 312A, 378Q, 380A, 382A, 434A (Shields et al., (2001) *Journal of Biological Chemistry*, 276(9):6591-6604), 252F, 252Y, 252W, 254T, 256Q, 256E, 256D, 433R, 434F, 434Y, 252Y/254T/256E, 433K/434F/436H (Dall'Acqua et al. (2002) *Journal of Immunology*, 169:5171-5180, Dall'Acqua et al., (2006), *Journal of Biological Chemistry* 281:23514-23524). See U.S. Pat. No. 8,367,805.

Modification of certain conserved residues in IgG Fc (I253, H310, Q311, H433, N434), such as the N434A variant (Yeung et al. (2009) *J. Immunol.* 182:7663), have been proposed as a way to increase FcRn affinity, thus increasing the half-life of the antibody in circulation. WO 98/023289. The combination Fc variant comprising M428L and N434S has been shown to increase FcRn binding and increase serum half-life up to five-fold. Zalevsky et al. (2010) *Nat. Biotechnol.* 28:157. The combination Fc variant comprising T307A, E380A and N434A modifications also extends half-life of IgG1 antibodies. Petkova et al. (2006) *Int. Immunol.* 18:1759. In addition, combination Fc variants comprising M252Y-M428L, M428L-N434H, M428L-N434F, M428L-N434Y, M428L-N434A, M428L-N434M, and M428L-N434S variants have also been shown to extend half-life. WO 2009/086320.

Further, a combination Fc variant comprising M252Y, S254T and T256E, increases half-life-nearly 4-fold. Dall'Acqua et al. (2006) *J. Biol. Chem.* 281:23514. A related IgG1 modification providing increased FcRn affinity but reduced pH dependence (M252Y-S254T-T256E-H433K-N434F) has been used to create an IgG1 construct ("MST-HN Abdeg") for use as a competitor to prevent binding of other antibodies to FcRn, resulting in increased clearance of that other antibody, either endogenous IgG (e.g. in an autoimmune setting) or another exogenous (therapeutic) mAb. Vaccaro et al. (2005) *Nat. Biotechnol.* 23:1283; WO 2006/130834.

Other modifications for increasing FcRn binding are described in Yeung et al. (2010) *J. Immunol.* 182:7663-7671; 6,277,375; 6,821,505; WO 97/34631; WO 2002/060919.

In certain embodiments, hybrid IgG isotypes may be used to increase FcRn binding, and potentially increase half-life. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A. See U.S. Pat. No. 8,629,113. A hybrid of IgG1/IgG2/IgG4 sequences has been generated that purportedly increases serum half-life and improves expression. U.S. Pat. No. 7,867,491 (sequence number 18 therein).

The serum half-life of the antibodies of the present invention can also be increased by pegylation. An antibody can be pegylated to, for example, increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0154316 by Nishimura et al. and EP 0401384 by Ishikawa et al.

Alternatively, under some circumstances it may be desirable to decrease the half-life of an antibody of the present invention, rather than increase it. Modifications such as I253A (Hornick et al. (2000) *J. Nucl. Med.* 41:355) and H435A/R, I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such a medical imaging. See also Kenanova et al. (2005) *Cancer Res.* 65:622. Other means to enhance clearance include formatting the antigen binding domains of the present invention as antibody fragments lacking the ability to bind FcRn, such as Fab fragments. Such modification can reduce the circulating half-life of an antibody from a couple of weeks to a matter of hours. Selective PEGylation of antibody fragments can then be used to fine-tune (increase) the half-life of the antibody fragments if necessary. Chapman et al. (1999) *Nat. Biotechnol.* 17:780. Antibody fragments may also be fused to human serum albumin, e.g. in a fusion protein construct, to increase half-life. Yeh et al. (1992) *Proc. Nat'l Acad. Sci.* (USA) 89:1904. Alternatively, a bispecific antibody may be constructed with a first antigen binding domain of the present invention and a second antigen binding domain that binds to human serum albumin (HSA). See Int'l Pat. Appl. Pub. WO 2009/127691 and patent references cited therein. Alternatively, specialized polypeptide sequences can be added to antibody fragments to increase half-life, e.g. "XTEN" polypeptide sequences. Schellenberger et al. (2009) *Nat. Biotechnol.* 27:1186; Int'l Pat. Appl. Pub. WO 2010/091122.

Additional Fc Variants

When using an IgG4 constant domain, it is usually preferable to include the substitution S228P, which mimics the hinge sequence in IgG1 and thereby stabilizes IgG4 molecules, e.g. reducing Fab-arm exchange between the therapeutic antibody and endogenous IgG4 in the patient being treated. Labrijn et al. (2009) *Nat. Biotechnol.* 27:767; Reddy et al. (2000) *J. Immunol.* 164:1925.

A potential protease cleavage site in the hinge of IgG1 constructs can be eliminated by D221G and K222S modifications, increasing the stability of the antibody. WO 2014/043344.

The affinities and binding properties of an Fc variant for its ligands (Fc receptors) may be determined by a variety of in vitro assay methods (biochemical or immunological based assays) known in the art including but not limited to, equilibrium methods (e.g., enzyme-linked immunosorbent assay (ELISA), or radioimmunoassay (RIA)), or kinetics (e.g., BIACORE SPR analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In still other embodiments, the glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. Bolt et al. (1993) *Eur. J. Immunol.* 23:403. See also Tao & Morrison (1989) *J. Immunol.* 143:2595 (using N297Q in IgG1 to eliminate glycosylation at position 297).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci.* (USA) 107:604).

Glycoengineering can also be used to modify the anti-inflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. See Nimmerjahn et al. (2008) *Ann. Rev. Immunol.* 26:513. Conversely, reduction in the proportion of antibodies having α2,6 sialylated carbohydrates may be useful in cases where anti-inflammatory properties are not wanted. Methods of modifying α2,6 sialylation content of antibodies, for example by selective purification of α2,6 sialylated forms or by enzymatic modification, are provided at U.S. Patent Application Publication No. 2008/0206246. In other embodiments, the amino acid sequence of the Fe region may be modified to mimic the effect of α2,6 sialylation, for example by inclusion of an F241A modification. WO 2013/095966.

III. Antibody Physical Properties

Antibodies described herein can contain one or more glycosylation sites in either the light or heavy chain variable region. Such glycosylation sites may result in increased immunogenicity of the antibody or an alteration of the pK of the antibody due to altered antigen binding (Marshall et al. (1972) *Ann. Rev. Biochem.* 41:673-702; Gala and Morrison (2004) *J. Immunol.* 172:5489-94; Wallick et al. (1988) *J. Exp. Med.* 168:1099-109; Spiro (2002) *Glycobiology* 12:43R-56R; Parekh et al. (1985) *Nature* 316:452-7; Mimura et al. (2000) *Mol Immunol* 37:697-706). Glycosylation has been known to occur at motifs containing an N-X-S/T sequence. In some instances, it is preferred to have an anti-huCD40 antibody that does not contain variable region glycosylation. This can be achieved either by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-CD40 antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) *Curr. Pharm. Biotechnol.* 3:361-71). Generally, it is preferred that the TM1 (the temperature of initial unfolding) be greater than 60° C., preferably greater than 65° C., even more preferably greater than 70° C. The melting point of an antibody can be measured using differential scanning calorimetry (Chen et al (2003) *Pharm Res* 20:1952-60; Ghirlando et al (1999) *Immunol Lett.* 68:47-52) or circular dichroism (Murray et al. (2002) *J. Chromatogr. Sci.* 40:343-9).

In a preferred embodiment, antibodies are selected that do not degrade rapidly. Degradation of an antibody can be measured using capillary electrophoresis (CE) and MALDI-MS (Alexander A J and Hughes D E (1995) *Anal Chem.* 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

IV. Nucleic Acid Molecules

Another aspect described herein pertains to nucleic acid molecules that encode the antibodies described herein. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and may or may not contain intronic sequences. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (hinge, CH1, CH2 and/or CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al. (1988) Science 242:423-426; Huston et al. (1988) Proc. Natl. Acad. Sci. (USA) 85:5879-5883; McCafferty et al., (1990) Nature 348:552-554).

V. Antibody Generation

Various antibodies of the present invention, e.g. those that compete with or bind to the same epitope as the anti-human CD40 antibodies disclosed herein, can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In one embodiment, the antibodies described herein are human monoclonal antibodies. Such human monoclonal antibodies directed against human CD40 can be generated using transgenic or transchromosomic mice carrying parts of the human immune system rather than the mouse system. These transgenic and transchromosomic mice include mice referred to herein as HUMAB mice and KM mice, respectively, and are collectively referred to herein as "human Ig mice."

The HUMAB mouse (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HUMAB mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. (USA) 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-huCD40 antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-CD40 antibodies described herein. For example, mice carrying both a human heavy chain transchromosome and a human light chain transchromosome, referred to as "TC mice" can be used; such mice are described in Tomizuka et al. (2000) Proc. Natl. Acad. Sci. (USA) 97:722-727. Furthermore, cows carrying human heavy and light chain transchromosomes have been described in the art (Kuroiwa et al. (2002) Nature Biotechnology 20:889-894) and can be used to raise anti-huCD40 antibodies described herein.

Additional mouse systems described in the art for raising human antibodies, e.g., human anti-huCD40 antibodies, include (i) the VELOCIMMUNE mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MEMO mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to human CD40, mice or transgenic or transchromosomal mice containing human immunoglobulin genes (e.g., HCo12, HCo7 or KM mice) can be immunized with a purified or enriched preparation of the CD40 antigen and/or cells expressing CD40, as described for other antigens, for example, by Lonberg et al. (1994) Nature 368(6474): 856-859; Fishwild et al. (1996) Nature Biotechnology 14: 845-851 and WO 98/24884. Alternatively, mice can be immunized with DNA encoding human CD40. Preferably, the mice will be 6-16 weeks of age upon the first infusion. For example, a purified or enriched preparation (5-50 μg) of the recombinant human CD40 antigen can be used to immunize the mice intraperitoneally. In the event that immunizations using a purified or enriched preparation of the CD40 antigen do not result in antibodies, mice can also be immunized with cells expressing CD40, e.g., a cell line, to promote immune responses.

Cumulative experience with various antigens has shown that the HUMAB transgenic mice respond best when initially immunized intraperitoneally (IP) or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-CD40 human immunoglobulin can be used for fusions. Mice can be boosted intravenously with antigen 3 days before sacrifice and removal of the spleen and lymph nodes. It is expected that 2-3 fusions for each immunization may need to be performed. Between 6 and 24 mice are typically immunized for each antigen. Usually, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to CD40

To generate hybridomas producing monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 nonsecreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

VI. Antibody Manufacture

Generation of Transfectomas Producing Monoclonal Antibodies to CD40

Antibodies of the present invention, including both specific antibodies for which sequences are provided and other, related anti-CD40 antibodies, can be produced in a host cell transfectoma using, for example, a combination of recombinant DNA techniques and gene transfection methods as is well known in the art (Morrison, S. (1985) Science 229: 1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, CA (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). Antibodies of the present invention can also be produced in glycoengineered strains of the yeast *Pichia pastoris*. Li et al. (2006) *Nat. Biotechnol.* 24:210.

Preferred mammalian host cells for expressing the recombinant antibodies described herein include Chinese Hamster Ovary (CHO cells) (including dhfr-CHO cells, described in Urlaub and Chasm, (1980) *Proc. Natl. Acad. Sci.* (USA) 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications. For example, C-terminal lysine residues are often missing from antibody heavy chains. Dick et al. (2008) *Biotechnol. Bioeng.* 100:1132. N-terminal glutamine residues, and to a lesser extent glutamate residues, are frequently converted to pyroglutamate residues on both light and heavy chains of therapeutic antibodies. Dick et al. (2007) *Biotechnol. Bioeng.* 97:544; Liu et al. (2011) *J. Biol. Chem.* 286:11211.

VII. Assays

Antibodies described herein can be tested for binding to CD40 by, for example, standard ELISA. Briefly, microtiter plates are coated with purified CD40 at 1-2 µg/ml in PBS, and then blocked with 5% bovine serum albumin in PBS. Dilutions of antibody (e.g., dilutions of plasma from CD40-immunized mice) are added to each well and incubated for 1-2 hours at 37° C. The plates are washed with PBS/Tween and then incubated with secondary reagent (e.g., for human antibodies, or antibodies otherwise having a human heavy chain constant region, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human CD40, but not to a control cell line that does not express CD40. Briefly, the binding of anti-CD40 antibodies is assessed by incubating CD40 expressing CHO cells with the anti-CD40 antibody at 1:20 dilution. The cells are washed and binding is detected with a PE-labeled anti-human IgG Ab. Flow cytometric analyses are performed using a FACScan flow cytometry (Becton Dickinson, San Jose, CA). Preferably, mice that develop the highest titers will be used for fusions. Analogous experiments may be performed using anti-mouse detection antibodies if mouse anti-huCD40 antibodies are to be detected.

An ELISA as described above can be used to screen for antibodies and, thus, hybridomas that produce antibodies that show positive reactivity with the CD40 immunogen. Hybridomas that produce antibodies that bind, preferably with high affinity, to CD40 can then be subcloned and further characterized. One clone from each hybridoma, which retains the reactivity of the parent cells (by ELISA), can then be chosen for making a cell bank, and for antibody purification.

To purify anti-CD40 antibodies, selected hybridomas can be grown in two-liter spinner-flasks for monoclonal antibody purification. Supernatants can be filtered and concentrated before affinity chromatography with protein A-sepharose (Pharmacia, Piscataway, NJ). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CD40 monoclonal antibodies bind to unique epitopes, each antibody can be biotinylated using commercially available reagents (Pierce, Rockford, IL). Biotinylated MAb binding can be detected with a streptavidin labeled probe. Competition studies using unlabeled monoclonal antibodies and biotinylated monoclonal antibodies can be performed using CD40 coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing CD40, flow cytometry can be used. Briefly, cell lines expressing membrane-bound CD40 (grown under standard growth conditions) are mixed with various concentrations of monoclonal antibodies in PBS containing 0.1% BSA at 4° C. for 1 hour. After washing, the cells are reacted with Phycoerythrin (PE)-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-huCD40 antibodies can be further tested for reactivity with the CD40 antigen by Western blotting. Briefly, cell extracts from cells expressing CD40 can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, MO).

Methods for analyzing binding affinity, cross-reactivity, and binding kinetics of various anti-CD40 antibodies include standard assays known in the art, for example, Biolayer Interferometry (BLI) analysis, and BIACORE surface plasmon resonance (SPR) analysis using a BIACORE 2000 SPR instrument (Biacore AB, Uppsala, Sweden).

In one embodiment, an antibody specifically binds to the extracellular region of human CD40. An antibody may specifically bind to a particular domain (e.g., a functional domain) within the extracellular domain of CD40. In certain embodiments, the antibody specifically binds to the extracellular region of human CD40 and the extracellular region of cynomolgus CD40. Preferably, an antibody binds to human CD40 with high affinity.

VIII. Bispecific Molecules

Antibodies described herein may be used for forming bispecific molecules. An anti-CD40 antibody, or antigen-binding fragments thereof, can be derivatized or linked to another functional molecule, e.g., another peptide or protein (e.g., another antibody or ligand for a receptor) to generate a bispecific molecule that binds to at least two different binding sites or target molecules. The antibody described herein may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule described herein, an antibody described herein can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, provided herein are bispecific molecules comprising at least one first binding specificity for CD40 and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies that can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci.* (USA) 82:8648). Other methods include those described in Paulus (1985) *Behring Ins. Mitt.* No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand×Fab fusion protein. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Compositions

Further provided are compositions, e.g., a pharmaceutical compositions, containing one or more anti-CD40 antibodies, or antigen-binding fragment(s) thereof, as described herein, formulated together with a pharmaceutically acceptable carrier. Such compositions may include one or a combination of (e.g., two or more different) antibodies, or immunoconjugates or bispecific molecules described herein. For example, a pharmaceutical composition described herein can comprise a combination of antibodies (or immunoconjugates or bispecifics) that bind to different epitopes on the target antigen or that have complementary activities.

In certain embodiments, a composition comprises an anti-CD40 antibody at a concentration of at least 1 mg/ml, 5 mg/ml, 10 mg/ml, 50 mg/ml, 100 mg/ml, 150 mg/ml, 200 mg/ml, or at 1-300 mg/ml or 100-300 mg/ml.

Pharmaceutical compositions described herein also can be administered in combination therapy, i.e., combined with other agents. For example, the combination therapy can include an anti-CD40 antibody described herein combined with at least one other anti-cancer and/or T-cell stimulating (e.g., activating) agent. Examples of therapeutic agents that can be used in combination therapy are described in greater detail below in the section on uses of the antibodies described herein.

In some embodiments, therapeutic compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient that can be combined with a carrier material to produce a single dosage form will vary depending upon the subject being treated, and the particular mode of administration. The amount of active ingredient that can be combined with a carrier material to produce a single dosage form will generally be that amount of the composition that produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months.

In some methods, two or more monoclonal antibodies with different binding specificities are administered simultaneously, in which case the dosage of each antibody administered falls within the ranges indicated. A therapeutic antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can optionally be administered a prophylactic regime, although in many immune-oncology indications continued treatment is not necessary.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CD40 antibody described herein preferably results in a decrease in severity of disease symptoms, an increase in frequency and duration of disease symptom-free periods, or a prevention of impairment or disability due to the disease affliction. In the context of cancer, a therapeutically effective dose preferably prevents further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like. Therapeutic efficacy may be observable immediately after the first administration of an agonistic anti-huCD40 mAb of the present invention, or it may only be observed after a period of time and/or a series of doses. Such delayed efficacy my only be observed after several months of treatment, up to 6, 9 or 12 months. It is critical not to decide prematurely that an agonistic anti-huCD40 mAb of the present invention lacks therapeutically efficacy in light of the delayed efficacy exhibited by some immune-oncology agents.

A therapeutically effective dose may prevent or delay onset of cancer, such as may be desired when early or preliminary signs of the disease are present. Laboratory tests utilized in the diagnosis of cancer include chemistries (including the measurement of soluble CD40 or CD40L levels) (Hock et al. (2006) *Cancer* 106:2148; Chung & Lim (2014) *J. Trans. Med.* 12:102), hematology, serology and radiology. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-huCD40 antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-huCD40 antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

X. Uses and Methods

The antibodies, antibody compositions and methods described herein have numerous in vitro and in vivo utilities involving, for example, enhancement of immune response by agonizing CD40 signaling. In a preferred embodiment, the antibodies described herein are human or humanized antibodies. For example, anti-huCD40 antibodies described herein can be administered to cells in culture, in vitro or ex vivo, or to human subjects, e.g., in vivo, to enhance immunity in a variety of diseases. Accordingly, provided herein are methods of modifying an immune response in a subject comprising administering to the subject an antibody, or antigen-binding fragment thereof, described herein such that the immune response in the subject is enhanced, stimulated or up-regulated.

Preferred subjects include human patients in whom enhancement of an immune response would be desirable. The methods are particularly suitable for treating human patients having a disorder that can be treated by augmenting an immune response (e.g., the T-cell mediated immune response). In a particular embodiment, the methods are particularly suitable for treatment of cancer in vivo. To achieve antigen-specific enhancement of immunity, anti-huCD40 antibodies described herein can be administered together with an antigen of interest or the antigen may already be present in the subject to be treated (e.g., a tumor-bearing or virus-bearing subject). When antibodies to CD40 are administered together with another agent, the two can be administered separately or simultaneously.

Also encompassed are methods for detecting the presence of human CD40 antigen in a sample, or measuring the amount of human CD40 antigen, comprising contacting the sample, and a control sample, with a human monoclonal antibody, or an antigen binding fragment thereof, that specifically binds to human CD40, under conditions that allow for formation of a complex between the antibody or fragment thereof and human CD40. The formation of a complex is then detected, wherein a difference complex formation between the sample compared to the control sample is indicative the presence of human CD40 antigen in the sample. Moreover, the anti-CD40 antibodies described herein can be used to purify human CD40 via immunoaffinity purification.

Given the ability of anti-huCD40 antibodies described herein to enhance co-stimulation of T cell responses, e.g., antigen-specific T cell responses, provided herein are in vitro and in vivo methods of using the antibodies described herein to stimulate, enhance or upregulate antigen-specific T cell responses, e.g., anti-tumor T cell responses.

$CD4^+$ and $CD8^+$ T cell responses can be enhanced using anti-CD40 antibodies. The T cells can be Teff cells, e.g., CD4+ Teff cells, CD8+ Teff cells, T helper (Th) cells and T cytotoxic (Tc) cells.

Further encompassed are methods of enhancing an immune response (e.g., an antigen-specific T cell response) in a subject comprising administering an anti-huCD40 antibody described herein to the subject such that an immune response (e.g., an antigen-specific T cell response) in the subject is enhanced. In a preferred embodiment, the subject is a tumor-bearing subject and an immune response against the tumor is enhanced. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is enhanced.

Further provided are methods for inhibiting growth of tumor cells in a subject comprising administering to the subject an anti-huCD40 antibody described herein such that growth of the tumor is inhibited in the subject. Also provided are methods of treating chronic viral infection in a subject comprising administering to the subject an anti-huCD40 antibody described herein such that the chronic viral infection is treated in the subject.

In certain embodiments, an anti-huCD40 antibody is given to a subject as an adjunctive therapy. Treatments of subjects having cancer with an anti-huCD40 antibody may lead to a long-term durable response relative to the current standard of care; long term survival of at least 1, 2, 3, 4, 5, 10 or more years, recurrence free survival of at least 1, 2, 3, 4, 5, or 10 or more years. In certain embodiments, treatment of a subject having cancer with an anti-huCD40 antibody prevents recurrence of cancer or delays recurrence of cancer by, e.g., 1, 2, 3, 4, 5, or 10 or more years. An anti-CD40 treatment can be used as a primary or secondary line of treatment.

These and other methods described herein are discussed in further detail below.

Cancer

Provided herein are methods for treating a subject having cancer, comprising administering to the subject an anti-huCD40 antibody described herein, such that the subject is treated, e.g., such that growth of cancerous tumors is inhibited or reduced and/or that the tumors regress. An anti-huCD40 antibody can be used alone to inhibit the growth of cancerous tumors. Alternatively, an anti-huCD40 antibody can be used in conjunction with another agent, e.g., other immunogenic agents, standard cancer treatments, or other antibodies, as described below.

Accordingly, provided herein are methods of treating cancer, e.g., by inhibiting growth of tumor cells, in a subject, comprising administering to the subject a therapeutically effective amount of an anti-huCD40 antibody described herein, or antigen-binding fragment thereof. The antibody may be a humanized anti-huCD40 antibody, a human chimeric anti-huCD40 antibody, or a humanized non-human anti-huCD40 antibody, e.g., a human, chimeric or humanized anti-huCD40 antibody that competes for binding with, or binds to the same epitope as, at least one of the anti-huCD40 antibodies specifically described herein.

Cancers whose growth may be inhibited using the antibodies of the invention include cancers typically responsive to immunotherapy. Non-limiting examples of cancers for treatment include squamous cell carcinoma, small-cell lung cancer, non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M 1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. The methods described herein may also be used for treatment of metastatic cancers, refractory cancers (e.g., cancers refractory to previous immunotherapy, e.g., with a blocking CTLA-4 or PD-1 antibody), and recurrent cancers.

An anti-huCD40 antibody can be administered as a monotherapy, or as the only immunostimulating therapy, or it can be combined with an immunogenic agent in a cancer vaccine strategy, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al. (1993) *Proc. Natl. Acad. Sci.* (USA) 90: 3539-43.

The study of gene expression and large scale gene expression patterns in various tumors has led to the definition of so called tumor specific antigens. Rosenberg, S A (1999) *Immunity* 10: 281-7. In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host. CD40 agonists can be used in conjunction with a collection of recombinant proteins and/or peptides expressed in a tumor in order to generate an immune response to these proteins. These proteins are normally viewed by the immune system as self antigens and are therefore tolerant to them. The tumor antigen can include the protein telomerase, which is required for the synthesis of telomeres of chromosomes and which is expressed in more than 85% of human cancers and in only a limited number of somatic tissues (Kim et al. (1994) *Science* 266: 2011-2013). Tumor antigen can also be "neo-antigens" expressed in cancer cells because of somatic mutations that alter protein sequence or create fusion proteins between two unrelated sequences (i.e., bcr-abl in the Philadelphia chromosome), or idiotype from B cell tumors.

Other tumor vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen that can be used in conjunction with CD40 inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) *Science* 278: 117-120).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) *Nature Medicine* 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with CD40 agonism to activate (unleash) more potent anti-tumor responses.

Agonism of CD40 can also be combined with standard cancer treatments (e.g., surgery, radiation, and chemotherapy). Agonism of CD40 can be effectively combined with chemotherapeutic regimes. In these instances, it may be possible to reduce the dose of chemotherapeutic reagent administered (Mokyr et al. (1998) *Cancer Research* 58: 5301-5304). An example of such a combination is an anti-huCD40 antibody in combination with decarbazine for the treatment of melanoma. Another example of such a combination is an anti-huCD40 antibody in combination with interleukin-2 (IL-2) for the treatment of melanoma. The scientific rationale behind the combined use of CD40 agonists and chemotherapy is that cell death, that is a consequence of the cytotoxic action of most chemotherapeutic compounds, should result in increased levels of tumor antigen in the antigen presentation pathway. Other combination therapies that may result in synergy with CD40 agonism through cell death are radiation, surgery, and hormone deprivation. Each of these protocols creates a source of tumor antigen in the host. Angiogenesis inhibitors can also be combined with CD40 agonists. Inhibition of angiogenesis leads to tumor cell death which may feed tumor antigen into host antigen presentation pathways.

The anti-huCD40 antibodies described herein can also be used in combination with bispecific antibodies that target Fcα or Fcγ receptor-expressing effectors cells to tumor cells (see, e.g., U.S. Pat. Nos. 5,922,845 and 5,837,243). Bispecific antibodies can be used to target two separate antigens. For example anti-Fc receptor/anti-tumor antigen (e.g., Her-2/neu) bispecific antibodies have been used to target macrophages to sites of tumor. This targeting may more effectively activate tumor specific responses. The T cell arm of these responses would be augmented by agonism of CD40. Alternatively, antigen may be delivered directly to DCs by the use of bispecific antibodies that bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include among others TGF-β (Kehrl et al. (1986) *J. Exp. Med.* 163: 1037-1050), IL-10 (Howard & O'Garra (1992) *Immunology Today* 13: 198-200), and Fas ligand (Hahne et al. (1996) *Science* 274: 1363-1365). Antibodies to each of these entities can be used in combination with anti-huCD40 antibodies to counteract the effects of the immunosuppressive agent and favor tumor immune responses by the host.

Anti-CD40 antibodies are able to substitute effectively for T cell helper activity. Ridge et al. (1998) *Nature* 393: 474-478. Activating antibodies to T cell costimulatory molecules such as CTLA-4 (e.g., U.S. Pat. No. 5,811,097), OX-40 (Weinberg et al. (2000) *Immunol* 164: 2160-2169), CD137/4-1BB (Melero et al. (1997) *Nature Medicine* 3: 682-685 (1997), and ICOS (Hutloff et al. (1999) *Nature* 397: 262-266) may also provide for increased levels of T cell activation. Inhibitors of PD1 or PD-L1 may also be used in conjunction with anti-huCD40 antibodies.

There are also several experimental treatment protocols that involve ex vivo activation and expansion of antigen specific T cells and adoptive transfer of these cells into recipients in order to stimulate antigen-specific T cells against tumor (Greenberg & Riddell (1999) *Science* 285: 546-51). These methods can also be used to activate T cell responses to infectious agents such as CMV. Ex vivo activation in the presence of anti-CD40 antibodies can increase the frequency and activity of the adoptively transferred T cells.

Chronic Viral Infections

In another aspect, the invention described herein provides a method of treating an infectious disease in a subject comprising administering to the subject an anti-huCD40 antibody, or antigen-binding fragment thereof, such that the subject is treated for the infectious disease.

Similar to its application to tumors as discussed above, antibody-mediated CD40 agonism can be used alone, or as an adjuvant, in combination with vaccines, to enhance the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, *Leishmania, Staphylococcus aureus, Pseudomonas aeruginosa*. CD40 agonism is particularly useful against established infections by agents such as HIV that present altered antigens over the course of the infections. These novel epitopes are recognized as foreign at the time of anti-human CD40 antibody administration, thus provoking a strong T cell response.

Some examples of pathogenic viruses causing infections treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods described herein include chlamydia, rickettsial bacteria, mycobacteria, staphylococci, streptococci, pneumonococci, meningococci and gonococci, *klebsiella, proteus, serratia, pseudomonas, legionella*, diphtheria, *salmonella*, bacilli, cholera, tetanus, botulism, anthrax, plague, leptospirosis, and Lyme disease bacteria.

Some examples of pathogenic fungi causing infections treatable by methods described herein include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods described herein include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

In all of the above methods, CD40 agonism can be combined with other forms of immunotherapy such as cytokine treatment (e.g., interferons, GM-CSF, G-CSF, IL-2), or bispecific antibody therapy, which provides for enhanced presentation of tumor antigens. See, e.g., Holliger (1993) *Proc. Natl. Acad. Sci. (USA)* 90:6444-6448; Poljak (1994) *Structure* 2:1121-1123.

Vaccine Adjuvants

Anti-huCD40 antibodies described herein can be used to enhance antigen-specific immune responses by co-administration of an anti-huCD40 antibody with an antigen of interest, e.g., a vaccine. Accordingly, provided herein are methods of enhancing an immune response to an antigen in a subject, comprising administering to the subject: (i) the antigen; and (ii) an anti-huCD40 antibody, or antigen-binding fragment thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Suitable routes of administering the antibody compositions (e.g., human monoclonal antibodies, multispecific and bispecific molecules and immunoconjugates) described herein in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, anti-huCD40 antibodies described herein can be co-administered with one or other more therapeutic agents, e.g., a cytotoxic agent, a radiotoxic agent or an immunosuppressive agent. The antibody can be linked to the agent (as an immuno-complex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, dacarbazine and cyclophosphamide hydroxyurea which, by themselves, are only effective at levels which are toxic or subtoxic to a patient. Cisplatin is intravenously administered as a 100 mg/ml dose once every four weeks and adriamycin is intravenously administered as a 60-75 mg/ml dose once every 21 days. Co-administration of anti-CD40 antibodies, or antigen binding fragments thereof, described herein with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells that would render them unreactive with the antibody.

Also within the scope described herein are kits comprising the antibody compositions described herein (e.g., human antibodies, bispecific or multispecific molecules, or immunoconjugates) and instructions for use. The kit can further contain at least one additional reagent, or one or more additional human antibodies described herein (e.g., a human antibody having a complementary activity that binds to an epitope in CD40 antigen distinct from the first human antibody). Kits typically include a label indicating the intended use of the contents of the kit. The term label includes any writing, or recorded material supplied on or with the kit, or that otherwise accompanies the kit.

Combination Therapies

In addition to the combinations therapies provided above, anti-CD40 antibodies described herein can also be used in combination therapy, e.g., for treating cancer, as described below.

The present invention provides methods of combination therapy in which an anti-huCD40 antibody is co-administered with one or more additional agents, e.g., antibodies, that are effective in stimulating immune responses to thereby further enhance, stimulate or upregulate immune responses in a subject.

Generally, an anti-huCD40 antibody described herein can be combined with (i) an agonist of another co-stimulatory receptor and/or (ii) an antagonist of an inhibitory signal on T cells, either of which results in amplifying antigen-specific T cell responses (immune checkpoint regulators). Most of the co-stimulatory and co-inhibitory molecules are members of the immunoglobulin super family (IgSF), and anti-CD40 antibodies described herein may be administered with an agent that targets a member of the IgSF family to increase an immune response. One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which include CD40 and CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTOR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR (see, e.g., Tansey (2009) *Drug Discovery Today* 00:1).

In another aspect, anti-huCD40 antibodies can be used in combination with antagonists of cytokines that inhibit T cell activation (e.g., IL-6, IL-10, TGF-β, VEGF; or other "immunosuppressive cytokines," or cytokines that stimulate T cell activation, for stimulating an immune response, e.g., for treating proliferative diseases, such as cancer.

The agonist anti-huCD40 antibodies and combination antibody therapies described herein may also be used in conjunction with other well known therapies that are selected for their particular usefulness against the indication being treated (e.g., cancer). Combinations of the agonist anti-huCD40 antibodies described herein may be used sequentially with known pharmaceutically acceptable agent(s).

For example, the agonist anti-huCD40 antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo21/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 (IDO1) inhibitor (e.g., INCB24360), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., AVASTIN), synthetic triterpenoids (see Hyer et al., *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), trastuzumab, cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSK3β inhibitors, IAP inhibitors and/or genotoxic drugs.

The agonist anti-huCD40 antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with agonist anti-huCD40 antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discoderomolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptophycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In cases where it is desirable to render aberrantly proliferative cells quiescent in conjunction with or prior to treatment with agonist anti-huCD40 antibodies described herein, hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™, can also be administered to the patient. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols well known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1

Generation of CD40/FcγR Humanized Mice

To generate an accurate and efficient model that can readily evaluate the activity of human anti-CD40 Fc variants and enable the selection of an optimized clinical candidate, we generated a unique mouse model humanized for CD40 and FcγRs. First, humanized CD40 mice on a mouse CD40-deficient background were generated. The expression pattern of the human CD40 BAC transgene on different immune cell populations in these mice were evaluated and found that human CD40 expression on blood B cells, dendritic cells, monocytes and macrophages, but not on T cell, neutrophils and NK cell populations is similar to the pattern found on human cells and their mouse orthologes (FIG. 1A).

Figure 2:
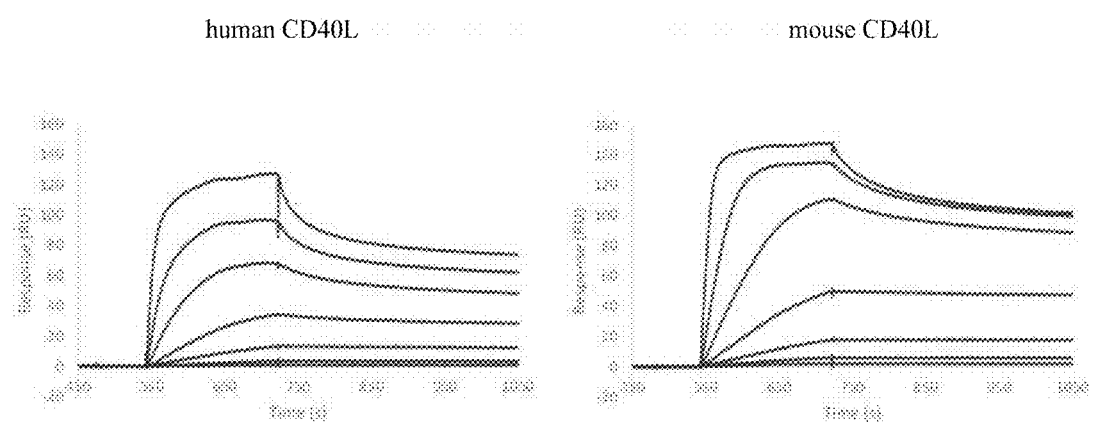
FIG. 2 shows the binding of hCD40 to mouse and human CD40L using SPR analysis with immobilized human CD40 and soluble human/mouse CD40L titrated from 33 to 0.5 nM.

The functionality of the huCD40 transgene in these mice, was verified by evaluating the formation of germinal centers (GC), a process that requires CD40 signaling (Basso et al. (2004) Blood 104, 4088-4096). While CD40$^{-/-}$ mice lost the ability to form a GC, this phenotype was restored upon the introduction of the huCD40 transgene FIG. 1B, mediated by the interaction of the huCD40 with the mouse CD40 ligand, which have similar binding kinetics and affinity to human CD40 ligand FIG. 2. CD40$^{-/-}$ mice have a deficient antigen-specific IgG response upon immunization, which was restored upon introduction of the huCD40 transgene FIG. 1C, confirming that hCD40 transgene functionally complements the mouse CD40 deficiency. Together, these data demonstrate that the humanized CD40 mice recapitulate the expression pattern and function of the human gene. To generate a mouse model in which fully human agonistic IgGs against human CD40 can be evaluated, these CD40 humanized mice were crossed to our previously described humanized FcγR mice (characterized in detail by (DiLillo and Ravetch (2015) Cell 161, 1035-1045; Smith et al., 2012 PNAS (USA) 109, 6181-6186) resulting in a strain of mice expressing the human CD40 and alpha chains of the FCGR1A, FCGR2AR131, FCGR2BI232, FCRG3AF158, and FCGR3B genes under the control of their endogenous human regulatory elements on an isogenic background deleted for the homologous mouse genes.

FcγRαnull mice have FcγR α chain deletion of Fcgr2b, Fcgr3, and Fcgr4, and are crossed to FcγRI−/− mice (Barnes et al., 2002 Immunity 16, 379-389. They were generated in a C57BL/6 background and characterized as previously described (Smith, et al. (2012) PHAS USA 109, 6181-6186). FcγR humanized mice (FcγRαnull, hFcγR1+, FcγRIIa$^{R131+}$, FcγRIIb$^+$, FcγRIIIa$^{F158+}$, and FcγRIIIb$^+$) generated and extensively characterized as previously described (Smith, et al. (2012) PNAS (USA) 109, 6181-6186). Human CD40 transgenic mice were generated on a C57BL/6 genetic background by pronuclear injection of linearized RP11-177B15 BAC DNA (Osoegawa, et al. (2001) Genome Research 11, 483-496) and were mated with CD40-knockout ("CD40$^{-/-}$") mice (The Jackson Laboratory) to obtain CD40$^{-/-}$huCD40$^{+/+}$ mice. CD40$^{-/-}$huCD40$^{+/+}$ mice were mated with FcγR humanized mice to obtain the humanized CD40 and FcγR mice (referred "hCD40/FcγR") containing the CD40$^{-/-}$hCD40$^+$Fcgra$^{-/-}$Fcgr1$^{-/-}$hFCGRI$^+$hFCGRIIA$^+$hFCGRIIB$^+$hFCGRIIIA$^+$hFCGRIIIB$^+$ genotype. hCD40/hFcRIIB$^+$/hFcRIIA$^+$ and hCD40/hFcRIIB$^+$/hFcRIIA$^-$ mice described in FIG. 4D were obtained during the mating described for the generation of hCD40/FcγR mice.

Example 2

OVA-Specific T Cell Response

Mice were immunized through i.p. injection with 2 μg of DEC-OVA(mIgG1-D265A) (produced as previously described by (Li and Ravetch (2011) Science 333, 1030-1034) in the presence or absence of 10 μg of anti-CD40 IgGs (except of ChiLob IgGs that were used at 40 μg/mice) with one of the various Fc's. Seven days later peripheral blood was collected and stained with FITC-conjugated anti-CD4, APC-conjugated anti-CD8a and PE-conjugated OVA peptide SIINFEKL H-2$^b$ tetramer (tet-OVA, Beckman Coulter) and analyzed on BD LSRForttesa.

Example 3

Flow Cytometry

Cell populations were defined by the following markers; DC (human: HLA-DR$^+$BDCA1$^+$CD209$^+$CD3$^-$CD14$^-$CD19$^-$CD59$^-$; mouse: CD11b$^+$CD11c$^+$MHC II$^+$F4/80$^-$), monocytes (human: CD14$^+$HLA-DR$^+$CD15$^-$; mouse: CD11b$^+$Ly6C$^+$F4/80$^-$CD11c$^-$), macrophages (human: CD14$^+$CD68+; mouse: CD11b+F4/80+Ly6C−Ly6G−), B cells (human: CD19+; mouse: B220+), T cells (human: CD3$^+$CD56$^-$; mouse: CD3), NK cells (human: CD16$^+$CD56$^+$CD3$^-$; mouse: NK1.1), neutrophils (human: CD15$^+$CD16$^+$CD49d$^-$; mouse: CD11b$^+$Ly6G$^+$Ly6C$^{int}$F4/80).

Example 4

H1N1 Immunization

Mice were immunized with recombinant influenza H1N1 (Sino Biological Inc.) in the presence of Alum as adjuvant. After 11 days blood was collected and analyzed for anti-influenza H1N1-specific IgG using standard ELISA protocol.

Example 5

SPR

All experiments were performed with a Biacore T100 surface plasmon resonance (SPR) system (Biacore, GE Healthcare), as previously described (Bournazos, et al., 2014, *Cell* 158, 1243-1253). Briefly, experiments were performed at 25 C in HBS-EP+ buffer (10 mM HEPES, pH 7.4; 150 mM NaCl; 3.4 mM EDTA; 0.005% (v/v) surfactant P20). For the measurement of the affinity of IgG subclass variants for FcγRs and CD40 recombinant IgGs were immobilized on Series S CM5 chips by amine coupling and soluble ectodomains of FcγRs or CD40 samples were injected through flow cells at different concentrations. For some FcγRs, the measurements were repeated in a reversed orientation while immobilizing the FcγR and injecting soluble IgGs. Background binding to blank immobilized flow cells was subtracted and affinity constants were calculated using BIAcore T100 evaluation software (GE Healthcare) using the 1:1 Langmuir binding model.

Example 6

SPR-Based Competition Assay

SPR competition experiments were performed on a Biacore T100 instrument using a running buffer of 10 mM sodium phosphate, 130 mM sodium chloride, 0.05% Tween 20, pH 7.1 at 25° C., on a surface consisting of hCD40-Fc immobilized on a CM5 sensor chip using standard amine coupling chemistry. Competition for binding to hCD40L-Fc was assessed using the "dual injection" function in the T100 control software, by injecting molecule 1 (parental antibody or CD40L), immediately followed by the same concentration of molecule 1, or a mixture of molecule 1 plus molecule 2. Binding responses were compared to a control injection of molecule 2 alone. All experiments were performed using 180 s association and dissociation times at 30 μl/min. The surface was successfully regenerated between cycles using two 15 s pulses of 10 mM glycine pH 1.5 at a flow rate of 30 μl/min.

Example 7

CD40 Binding ELISA

Binding specificity and affinity of IgG subclasses were determined by ELISA using recombinant CD40 (Sino Biological Inc.). ELISA plates (Nunc) were coated overnight at 4C with recombinant extracellular domain of human CD40 (1 μg/well). All sequential steps were performed at room temperature. After being washed, the plates were blocked for 1 hr with PBS/2% skim milk and were subsequently incubated for 1 h with serially diluted IgGs (1:3 consecutive dilutions in PBS/2% skim milk). After washing, plates were incubated for 1 hr with HRP-conjugated anti-human IgG (Jackson ImmunoResearch). Detection was performed using two-component peroxidase substrate kit (KPL) and reactions stopped with the addition of 1 M phosphoric acid. Absorbance at 405 nm was immediately recorded using a SpectraMax Plus spectrophotometer (Molecular Devices) and background absorbance from negative control samples was subtracted.

Example 8

Generation and Production of Anti-CD40 Fc Variants

The variable heavy and light regions of anti-human CD40 Ab clone 21.4.1 (U.S. Pat. No. 7,338,660) were synthesized (Genwize) and cloned into mammalian expression vectors with human IgG1, human IgG2, or human kappa Fc backbones, as previously described (Li and Ravetch (2011) *Science* 333, 1030-1034). For the generation of Fc domain variants of human IgG1 (N297A, S267E, S267E/L328F, G237D/P238D/P271G/A330R, G237D/P238D/H268D/P271G/A330R) and human IgG2 (C127S, C232S), site-directed mutagenesis using specific primers was performed based on the QuikChange site-directed mutagenesis Kit II (Agilent Technologies) according to manufacturer's instructions. Mutated plasmid sequences were validated by direct sequencing (Genewiz).

Antibodies were generated by transient transfection of HEK293T cells (ATCC), purified using Protein G Sepharose 4 Fast Flow (GE Healthcare), dialyzed in PBS, and sterile filtered (0.22 mm), as previously described (Nimmerjahn, et al. (2005) *Immunity* 23, 41-51). Purity was assessed by SDS-PAGE and Coomassie staining, and was estimated to be >90%. Abs used for in vivo experiments were quantified for endotoxin (LPS) contamination by the Limulus Amebocyte Lysate (LAL) assay and verified to have levels <0.1 EU/μg. Polyclonal human IgG was were purchased from Bio X Cell.

Example 9

Tumor Challenge and Treatment

MC38 cells ($2 \times 10^6$) were implanted subcutaneously and tumor volumes were measured every 2-3 days with an electronic caliper and reported as volume using the formula $(L_1^2 \times L_2)/2$, whereas $L_1$ is the shortest diameter and $L_2$ is the longest diameter. 7 days after tumor inoculation, mice were randomized by tumor size (day 0) and received intraperitoneal (i.p) injection of 200 μg anti-CD40 or control IgGs. Mice received an additional 200 μg of IgG treatment at days 3. For the B16 lung metastasis model, mice were injected intravenously with $1 \times 10^6$ B16-F10 cells and treated with 40 μg of the indicated Abs on days 1 and 4 after tumor cell injection. On day 14 lungs were harvested and analyzed for the presence of surface metastasis foci by using a dissecting microscope.

Example 10

Generation of Human Anti-CD40-Fc-Variant Clinical Candidates

To test whether the in vivo activity of human IgGs targeting human CD40 requires interaction with huFcγRIIB and determine if such interactions can be further engineered to optimize the activity of the parent antibody, the variable regions of anti-CD40 clone 2141 (CP-870,893, originally an IgG2 isotype) were cloned into Fc-modified Abs with differential capacity to engage human FcγRs. These include wild type human IgG1 and a series of mutated IgG1s with increased binding affinities to hu FcγRIIB. ELISA FIG. 1D and SPR (Table 3) confirmed that the different Fc domains introduced into 2141 Abs did not alter either their binding specificity or their affinity to human CD40. Table 4 summarizes the affinities of different Fc variants of clone 2141 to recombinant huFcγRI, hFcγRIIA, huFcγRIIB, and huFcγR IIIA, as evaluated by SPR.

TABLE 3

Affinities of 21.4.1 Fc variants to human CD40

| Fc Variant | Ka (1/Ms) | Kd (1/s) | KD (M) |
| --- | --- | --- | --- |
| IgG1 | $5.973*10^4$ | $1.189*10^{-3}$ | $1.991*10^{-8}$ |
| IgG1-N297A | $5.234*10^4$ | $1.161*10^{-3}$ | $2.219*10^{-8}$ |
| IgG1-S267E | $4.999*10^4$ | $1.155*10^{-3}$ | $2.309*10^{-8}$ |
| IgG1-S267E/L328F | $4.232*10^4$ | $1.159*10^{-3}$ | $2.738*10^{-8}$ |
| IgG1-G237D/P238D/P271G/A330R (V9) | $4217*10^4$ | $1.129*10^{-3}$ | $2.678*10^{-8}$ |
| IgG1-G237D/P238D/H268D/P271G/A330R (V11) | $4.1*10^4$ | $1.125*10^{-3}$ | $2.743*10^{-8}$ |
| IgG2 | $3.486*10^4$ | $1.081*10^{-3}$ | $3.101*10^{-8}$ |
| IgG2-C232S (IgG2A) | $3.515*10^4$ | $1.088*10^{-3}$ | $3.095*10^{-8}$ |
| IgG2-C1.27S (IgG2B) | $3.549*10^4$ | $1.096*10^{-3}$ | $3.088*10^{-8}$ |

Binding constants were obtained by SPR analysis with immobilized IgGs and soluble CD40.

TABLE 4

Affinities of 21.4.1 Fc variants to human FcγRs

| | Inhibitory | | Activating | | | | | |
| --- | --- | --- | --- | --- | --- | --- | --- | --- |
| | hFcγRIIB | | hFcγRI | | hFcγRIIA$^{R131}$ | | hFcγRIIIA$^{F158}$ | |
| Fc variant | $K_D$ (M) | Fold | $K_D$ (M) | Fold | $K_D$ (M) | Fold | $K_D$ (M) | Fold |
| IgG wild type | $3.01 \times 10^{-6}$ | 1 | $5.17 \times 10^{-9}$ | 1 | $1.16 \times 10^{-6}$ | 1 | $6.7 \times 10^{-6}$ | 1 |
| N297A | n.d.b | NA | n.d.b | NA | n.d.b | NA | n.d.b | NA |
| SE | $8.33 \times 10^{-8}$ | 30.2 | $2.6 \times 10^{-9}$ | 1.1 | $9.8 \times 10^{-8}$ | 15.8 | n.d.b | NA |
| SELF | $4.31 \times 10^{-8}$ | 69.8 | $3.68 \times 10^{-9}$ | 1.4 | $1.77 \times 10^{-8}$ | 65.5 | n.d.b | NA |
| V9 | $9.39 \times 10^{-8}$ | 32 | $5.78 \times 10^{-7}$ | 0.009 | $4.11 \times 10^{-6}$ | 0.28 | n.d.b | NA |
| V11 | $3.15 \times 10^{-8}$ | 95.6 | $2.3 \times 10^{-7}$ | 0.022 | $3.88 \times 10^{-6}$ | 0.3 | n.d.b | NA |
| IgG2 | $<10^{-5}$ | NA | n.d.b | NA | $<10^{-5}$ | NA | $<10^{-5}$ | NA |

Binding constants were obtained by SPR analysis.
Fold = $K_D$(IgG1)/$K_D$(Fc variant)
n.d.b, no detectable binding;
NA, not applicable.
$K_D$ values and fold changes compared to wild type IgG1 for the SE mutant are from references (smith et al and Chu et al 2008).

Example 11

FcγR-Engagement is Required for the In Vivo Activity of Human Anti-CD40 mAbs

Figures 3A, 3B:
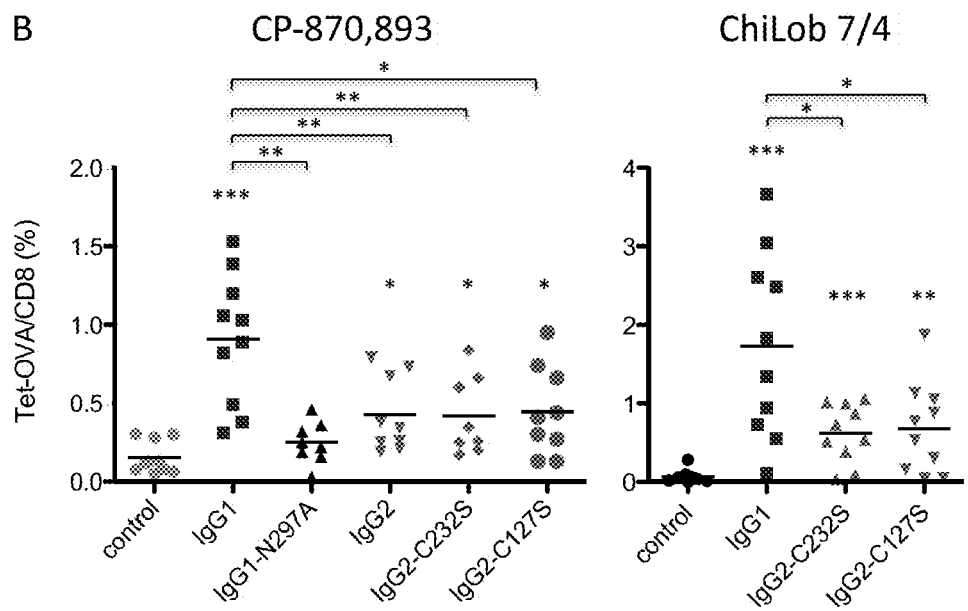
FIGS. 3A and 3B shows that human CD40 mAbs requires FcγR-engagement for in vivo activity.

While the IgG1 isotype has relatively high affinity interactions with all human FcγRs, the IgG2 isotype of CP-870,893 has very low binding affinities to human FcγRs, with the exception of the FcγRIIA$^{H131}$ (FIG. 3A and Table 4). The efficacy of the IgG1 and IgG2 isotypes of anti-CD40 in vivo in the context of human FcγRs, was compared by testing their ability to activate and expand T cells in the humanized CD40/FcγR model. Ovalbumin (OVA) was delivered to dendritic cells by the chimeric anti-DEC205 Ab conjugated to OVA ("DEC-OVA" (Li and Ravetch (2011) Science 333, 1030-1034)) together with either human IgG1-Fc, IgG2-Fc, or N297A Fc-null subclasses of CP-870,893 anti-CD40 mAb, and monitored for the presence of OVA-specific T cells in the circulation after 7 days (FIG. 3B). While both IgG1 and IgG2 isotypes had adjuvant effects on T cell activation, IgG1 resulted in a significantly higher T cell response as compared to the IgG2 isotype of the same anti-CD40 clone. The activity of IgG1 was completely reversed by introducing the N297A mutation, which prevents binding to FcγRs, implying that FcγR-engagement is required for the agonistic activity of the anti-CD40 IgG1. The significant activity of IgG2 was lost when tested as deglycosylated form that has reduced binding affinity to FcγRIIb compared to wild type IgG2. This implies on FcγR-dependent activity of anti-CD40 IgG2 as well and suggesting that the relatively reduced activity of IgG2 compared to IgG1 isotype may be explained by its low binding affinities to human FcγRs. In contrast to that conclusion, the agonistic activity of an anti-CD40 antibody of the IgG2 subclass has been proposed to be FcγR-independent and the result of the unique configuration of the IgG2 hinge (White, et al. (2015) Cancer cell 27, 138-148), mediated by shuffled disulfide bonds between the IgG2 hinge and CH1 regions. To test that possibility, specific cysteines of CP-870,893 were mutated, which resulted in locked conformational forms—the classical Y conformation "IgG2-A" and the more compact conformation "IgG2-B" obtained by C232S and C127S mutations, respectively (Allen et al., 2009, Biochemistry 48, 3755-3766). Both forms of IgG2 resulted in activity similar to wild type IgG2, implying that the hinge region conformation does not dictate the in vivo agonistic activity of the IgG2 isotype of this Ab clone in the context of human FcγRs. Moreover, the in vivo agonist activity of the IgG2-A and IgG2-B forms of CP-870,893 in human CD40 transgenic mice on either a mouse or human FcγR background were compared and found that in the mouse FcγR background only the IgG2-B form is active while in the human FcγR background both forms have significant and similar activity. The data obtain for the CP-870,893 Abs is supported further by the similar hierarchy in agonistic activity observed for the IgG1 and the 2A and 2B forms of IgG2 subclass of ChiLob 7/4, another agonistic human CD40 Ab clone which recognizes an epitope distinct from 2141. While the IgG2 subclass of ChiLob 7/4 was reported to have superior potency compared to its IgG1 form in the absence or presence of mouse FcγRs, we also observed that for this clone, in the presence of human FcγRs, the IgG1 subclass is superior to IgG2, and that both IgG2 conformational forms have similar activity. As observed for CP-870,893, when tested in huCD40/mFcγR mice, only the IgG2-B form is active and results in significant enhanced activity as compared to IgG2-A.

These data indicate that in the physiological context of human FcγRs, agonistic, human anti-CD40 IgGs depend on FcγR-engagement but not on their hinge-conformation for their in vivo activity. Importantly, the data highlights the advantage of using the humanized FcγR mouse model in order to appropriately study human IgGs activity. By considering the interaction of human IgG with human FcγRs, these mice avoid the confounding results that can be generated by using human IgGs in models carrying mouse FcγRs.

Example 12

Optimized Activity of Anti-CD40 Human IgGs Achieved by Fe Variants Enhanced for FcγRIIB- but not FcγR IIA-Binding We next determined whether increasing the binding interactions between human anti-CD40 antibodies and hFcγRIIB will result in increased in vivo efficacy. The binding affinity and selectivity of human IgGs to hFcγRIIB can be increased by mutagenesis of their Fc domain. Fc variants of CP-870,893 carrying the point mutations S267E (SE) and S267E/L328F (SELF) (Chu et al. (2008) *Molecular Immunology* 45, 3926-3933) result with 30- and 70-fold increased binding affinity to hFcγRIIB, respectively FIG. 4A and Table 4). When administered to the humanized FcγR/CD40 mice, these Fc variants resulted in small but significant increases in their ability to activate T cells in vivo as compared to both the wild type IgG1 and IgG2 variants of CP-870,893 FIG. 4B).

Due to the sequence and structural similarity between hFcγRIIA and hFcγRIIB, the SE and SELF mutations also result in increased binding affinity to the activating hFcγRIIA. Therefore, despite an increase in their binding affinity to the inhibitory hFcγRIIB, the FcγRIIA/FcγRIIB binding affinity ratio of these mutated IgGs is similar to that of wild type IgG1 and were thus predicted to result with limited increased activity of this subclass as was observed FIG. 4B. To optimize the Fc-engagement of FcγRIIB in the absence of FcγRIIA, we generated Fe variants of CP-870,893 with the recently described mutations, G237D/P238D/P271G/A330R (V9) and G237D/P238D/H268D/P271G/A330R (V11), which enhance binding affinity specifically to hFcγRIIB but not to hFcγRIIA (Mimoto et al., (2013) *PEDS* 26, 589-598). V9-CP-870,893 and VII-CP-870,893 Fc variants result with 32- and 97-fold increased binding affinity to hFcγRIIB and about 3-fold decreased binding affinity to hFcγRIIA$^{R131}$ FIG. 4A and Table 4). Both V9 and V11 Fc variants have significantly improved in vivo activity compared to the IgG2 subclass of CP-870,893 (IgG2), and its SE-, and SELF-Fc variants enhanced for both hFcγRIIB and hFcγRIIA. The 2141-V 11 variant results in 25-fold increase in T cell activation compared to CP-870,893-IgG2, and 5-fold increase compared to the activity obtained by the SELF variant FIG. 4B. A similar hierarchy was observed for CP-870,893 Fc variants when change in body weight was determined after antibody administration FIG. 5A. While all Fc variants tested resulted in statistically significant decreases in body weight after a single injection of anti-CD40, the group injected with V11-CP-870,893 had the most significant reduction.

We analyzed the pharmacokinetic (PK) properties of these Fc variants to test whether their differential FcγR binding leads to differential PK clearance rates that can account for their differential agonistic activities. SELF and V11 Fc variants of CP-870,893 were found to have a faster clearance rate than the IgG2 subclass (FIG. 4B), presumably a result of their enhanced FcRIIB binding activity. However, despite the fact that SELF and V11 have faster clearance rates, they display superior agonistic activity compared to IgG2. Similarly, despite the similar PK properties of SELF and V11, V 11 is a superior agonist compared to SELF. It is therefore excluded that the possibility that different PK properties of these Fc variants account for their agonistic activity.

Figures 4A, 4B, 4C, 4D:
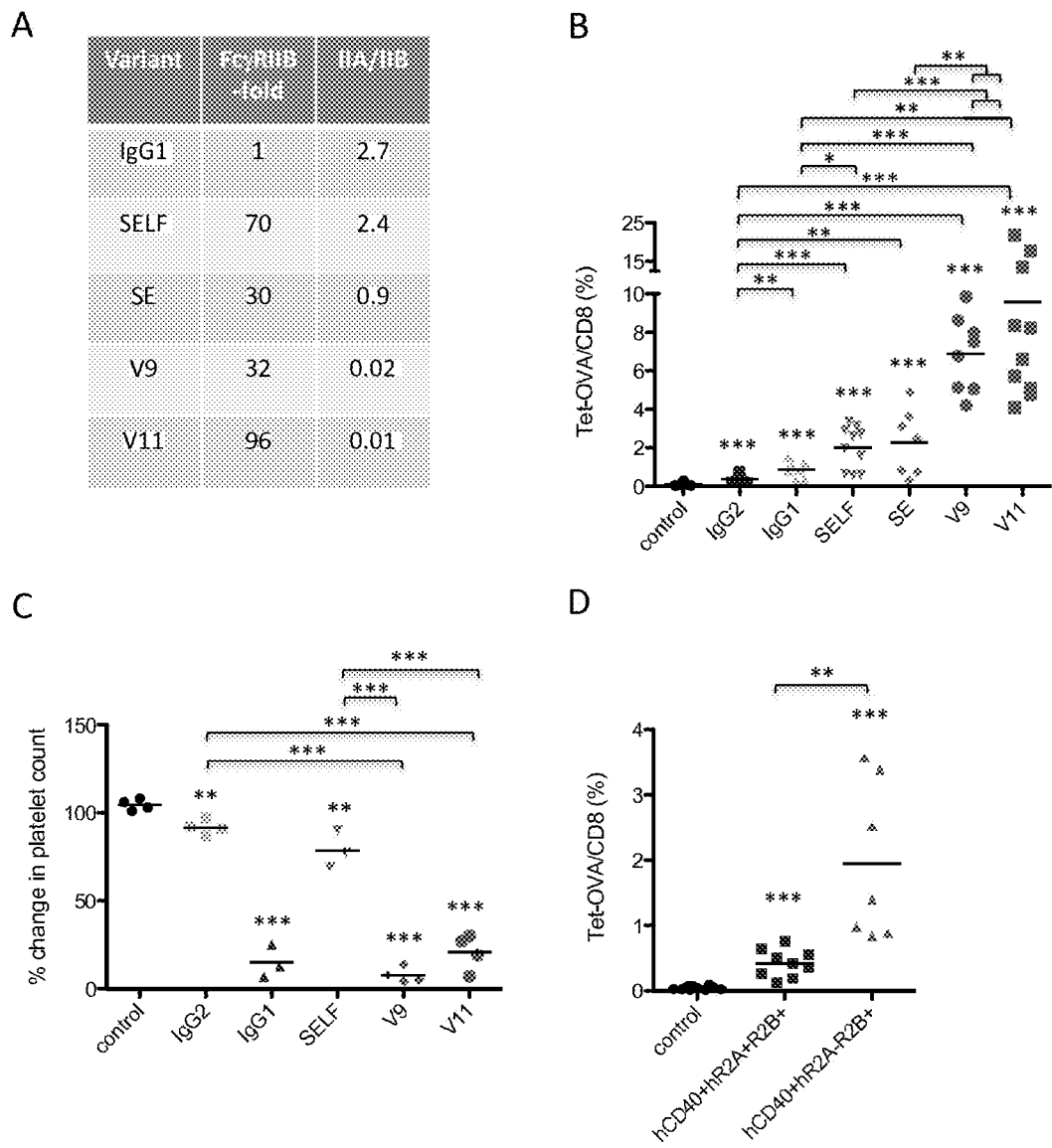
FIGS. 4A, 4B, 4C and 4D shows increased activity of CP-870,893 by Fc-engineering for FcγRIIB specific enhancement.
Figures 5A, 5B:
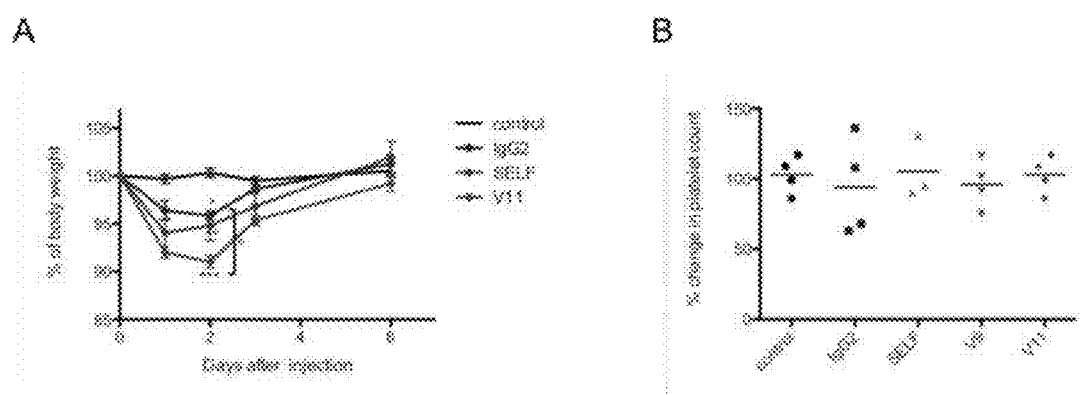
FIGS. 5A and 5B shows increased activity of CP-870,893 by Fc-engineering for FcγRIIB specific enhancement.

The influence of hFcγRIIA-engagement on the activity of CP-870,893, was evaluated by comparing its activity in mice transgenic for human CD40 and FcγRIIB, but not for FcγRIIA or mice transgenic to human CD40, FcγRIIB, and FcγRIIA (FIG. 4C). The T cell activation potency of CP-870,893-IgG2 is significantly enhanced in the absence of FcγRIIA, indicating the negative role of FcγRIIA-engagement on the agonistic activity of this anti-CD40 mAb.

The invention demonstrates that engineering CP-890,873 for enhanced hFcγRIIB-engagement while keeping a low FcγRIIA/FcγRIIB binding ratio results in optimized in vivo agonistic activity of human anti-CD40 IgGs.

Increased immunostimulatory activity by selective enhancement of FcγRIIB binding was demonstrated for 2141 (CP-870,893) mAb that does not block the binding of hCD40 to CD40L, demonstrating that agonist, human anti-CD40 mAbs can be optimized by selective enhancement of FcγRIIB-binding through Fc engineering independent of their binding epitopes and their ability to cross block CD40L binding to CD40.

The importance of FcγR interactions for the most potent human CD40 mAb was demonstrated in the clinic, among others, and how selective manipulation of FcγR-interactions by Fe-engineering enhances the potency of these drugs. These conclusions were made possible through the use of a representative in vivo model that faithfully recapitulates the diversity and cell type specificity of the human FcγR system.

This invention also refutes the notion that the epitope specificity of agonistic CD40 mAb determines its FcγR-requirements (FcγR-independent vs, -dependent, respectively) for activity. CP-870,893, ChiLob 7/4 does not compete with CD40L binding, but proved to be FcγR-dependent for their optimal activity in vivo.

Different modes-of-action can be observed between different mAb clones although they share the same target molecule. For example, it was recently observed that antagonistic PD-1 mAbs have the potential to deliver FcγRIIB-dependent agonism based on their epitope specificity (Dahan et al. (2015) *Cancer cell* 28, 285-295). Although mouse models can be very informative for evaluating mAb activity, translating of mAb activity in the mouse to the human therapeutic is not straightforward and therapeutic mechanisms observed for a mouse mAb can be altered while developing the homologous human IgGs. By humanizing both CD40 and FcγRs, a mouse model was generated that enables in vivo evaluation of clinical products by considering the activity mediated by both their Fab and Fe domains. These mice allow for "lead" selection among a panel of human CD40 mAbs based on their in vivo agonistic potency. A similar approach should be used for the generation of mice humanized for other therapeutic targets on the huFcγR background for optimal selection of additional immunomodulatory mAbs.

Although improved agonistic activity is mediated by Fc variants enhanced for both FcγRIIA and FcγRIIB binding (e.g. by S267E or S267E/L328F Fc mutations), their potency is limited by their enhanced binding to the activating FcγR IIA. Therefore, Fc variants with selective enhancement in binding solely to the inhibitory FcγRIIB have been indicated by this study as the most potent CD40 mAb derivatives. Lack of activity of mouse CD40 mAbs carrying the IgG2a subclass that preferentially binds activating FcγRs is associated with depletion of CD40 expressing cells (Li and Ravetch (2011) *Science* 333, 1030-1034). Since human FcγRIIIA, but not FcγR IIA, mediates in vivo depletion by mAbs (DiLillo and Ravetch (2015) *Cell* 161, 1035-1045), and the S267E or S267E/L328F mutants are enhanced to FcγRIIA but not FcγRIIIA, the reduced potency of the CD40 mAb mediated by FcγRIIA-engagement is not through depletion of CD40 expressing cells. The mechanism that accounts for this inhibitory effect by FcγRIIA is the subject of our ongoing investigations. Histidine (H)/arginine (R) polymorphism at position 131 of FcγRIIA dictates its binding affinity to IgG2, FcγRIIa$^{H131}$ has about 5-times higher affinity to IgG2 than FcγRIIa$^{R131}$ (van Sorge et al. (2003) *Tissue Antigens* 61, 189-202). Due to the inhibitory effect of FcγRIIA on the activity of CP-870,893, patients carrying the FcγRIIA$^{131H/H}$ genotype may have a reduced response to CP-870,893 treatment. Humanized mice carry the FcγRIIA$^{131R/R}$ genotype but an FcγRIIA$^{131H/H}$ strain is being generated so that the contribution of FcγRIIA allele polymorphism to the activity of anti-CD40 mAbs can be elucidated.

Example 13

V11 Fc Variant of Anti-CD40 Ab has Superior Anti-Tumor Activity

Whether the increased agonistic activity observed for the FcγRIIB-enhanced mutated Fc variants can be translated into increased anti-tumor activity of anti-CD40 mAbs was evaluated. Humanized CD40/FcγR mice were inoculated with the syngeneic MC38 colon adenocarcinoma tumors and treated with 2141-IgG2, -SELF, and -V11 Fc variants of 2141 anti-CD40 agonistic mAb (FIG. 6A). Treatments with both IgG2 (CP-870,893) and SELF Fc variants results in similar antitumor effects (about 65% reduction in tumor volume compared to untreated control, and 20% to 33% of tumor free mice, respectively). However, treatment with the V 11 Fc variant results in a dramatically improved antitumor response and complete recovery from tumors of all the mice in that group. A similar trend was observed using the B16 metastatic melanoma model in which a statistically significant reduction in the number of lung metastases was observed only in mice treated with V11 but not with SELF or IgG2 Fc variants FIG. 6B. These data indicate that the antitumor activity of CP-870,893 can be enhanced by Fc engineering of the antibody to provide selective enhancement of FcγRIIB-engagement and highlight the V11 Fc variant of this mAb clone as the optimal clinical candidate.

The unique hinge conformation of the human IgG2 isotype has recently reported to enhance the agonistic activity of CD40 mAbs in an FcγR-independent manner. It was therefore suggested that the superior agonistic activity observed for CP-870,893 is due to its IgG2 isotype compared the IgG1 isotype of the other agonistic CD40 Ab in clinical evaluations, ChiLob 7/4 and SGN40. When ChiLob 7/4 and SGN40 were generated as IgG2, they resulted in enhanced potency compared to their original IgG1 isotype (White et al. (2015) *Cancer cell* 27, 138-148). A drawback of that study is that the mAbs were evaluated only in the presence (or absence) of mouse FcγRs and their isotype-dependent potency in the correct context of human FcγRs was not evaluated. Here we demonstrated that using ChiLob 7/4 as IgG2 results in reduced activity compared to IgG1 in the context of human FcγRs. We further evaluated the activity of IgG1 vs IgG2 subclasses, including the 2A and 2B forms of IgG2, of both CP-870,893 and ChiLob 7/4 and found that IgG1 is more potent than IgG2 and its activity is FcγR-dependent. We therefore conclude that the superior agonistic activity of anti-CD40 human IgG2 observed in mice is not relevant to its clinical activity in humans. Moreover, the relatively high potency of CP-870,893 compared to the other CD40 mAbs is not a result to the IgG2 isotype and is likely the result of the mAb recognition of a unique specific agonistic epitope. Finally, selective enhancement for FcγRIIb-binding is by far the most efficient strategy to enhance the potency of CD40 mAb agonism.

TABLE 2

Summary of Sequence Listing

| SEQ ID | Description |
|---|---|
| 1 | Human CD40 (2141) Heavy Chain |
| 2 | Human CD40 Light Chain[1] |
| 3 | N297A Heavy Chain |
| 4 | SE Heavy Chain |
| 5 | SELF Heavy Chain |
| 6 | V9 Heavy Chain |
| 7 | V11 Heavy Chain |
| 8 | 2141-IgG2-Heavy chain |
| 9 | 2141-IgG2 C127S-Heavy chain |
| 10 | 2141-IgG2 C232S-Heavy chain |
| 11 | human CD40 (NP_001241.1), |
| 12 | human CD40L (NP_000065.1) |
| 13 | Signal Sequence |

[1]The light chain sequences for all 2141 (CP-870,893) Fc variants are identical to the sequence of SEQ ID NO: 2.

SEQ ID NO: 1

2141-IgG1 Heavy chain

Q V Q L V Q S G A E V K K P G A S V K V S C K A S G Y T F T G Y Y M H W V R Q A P

G Q G L E W M G W I N P D S G G T N Y A Q K F Q G R V T M T R D T S I S T A Y M E L

N R L R S D D T A V Y Y C A R D Q P L G Y C T N G V C S Y F D Y W G Q G T L V T V S

S A T T K G P S V F P L A P S S K S T S G G T A A L G C L V K D Y F P E P V T V S W N

S G A L T S G V H T F P A V L Q S S G L Y S L S S V V T V P S S S L G T Q T Y I C N V N

```
HKPSNTKVDKRVEPKSCDKTHTCPPCPAPELLGGPSVFLFPPKP
KDTLMISRTPEVTCVVVDVSHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK
                                                    SEQ ID NO: 2
2141- IgG1 Light chain
DIQMTQSPSSVSASVGDRVTITCRASQGIYSWLAWYQQKPGKA
PNLLIYTASTLQSGVPSRFSGSGSGTDFTLTISSLQPEDFATYYC
QQANIFPLTFGGGTKVEIKRTVAAPSVFIFPPSDEQLKSGTASV
VCLLNNFYPREAKVQWKVDNALQSGNSQESVTEQDSKDSTYS
LSSTLTLSKADYEKHKVYACEVTHQGLSSPVTKSFNRGEC
                                                    SEQ ID NO: 3
2141-IgG1 N297A Heavy chain
QVQLVQSGAEVKKPGASVKVSCKASGYTFTGYYMHWVRQAP
GQGLEWMGWINPDSGGTNYAQKFQGRVTMTRDTSISTAYMEL
NRLRSDDTAVYYCARDQPLGYCTNGVCSYFDYWGQGTLVTVS
SATTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKRVEPKSCDKTHTCPPCPAPELLGGPSVFLFPPKP
KDTLMISRTPEVTCVVVDVSHEDPEVKFNWYVDGVEVHNAKT
KPREEQYASTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK
                                                    SEQ ID NO: 4
2141-IgG1 S267E - Heavy chain
QVQLVQSGAEVKKPGASVKVSCKASGYTFTGYYMHWVRQAP
GQGLEQMGWINPDSGGTNYAQKFQGRVTMTRDTSISTAYMEL
NRLRSDDTAVYYCARDQPLGYCTNGVCSYFDYWGQGTLVTVS
SATTKGPSVFPLAPSSKSTSGGTAALGCLVKDYFPEPVTVSWN
SGALTSGVHTFPAVLQSSGLYSLSSVVTVPSSSLGTQTYICNVN
HKPSNTKVDKRVEPKSCDKTHTCPPCPAPELLGGPSVFLFPPKP
KDTLMISRTPEVTCVVVDVEHEDPEVKFNWYVDGVEVHNAKT
KPREEQYNSTYRVVSVLTVLHQDWLNGKEYKCKVSNKALPAP
IEKTISKAKGQPREPQVYTLPPSRDELTKNQVSLTCLVKGFYPS
DIAVEWESNGQPENNYKTTPPVLDSDGSFFLYSKLTVDKSRWQ
QGNVFSCSVMHEALHNHYTQKSLSLSPGK
                                                    SEQ ID NO: 5
2141-IgG1 S267E/L328F - Heavy chain
QVQLVQSGAEVKKPGASVKVSCKASGYTFTGYYMHWVRQAP
GQGLEWMGWINPDSGGTNYAQKFQGRVTMTRDTSISTAYMEL
NRLRSDDTAVYYCARDQPLGYCTNGVCSYFDYWGQGTLVTVS
SATTKGPSVFPLAPSSKSTSGGTAALGCLVKDYFPEPVTVSWN
```

```
S G A L T S G V H T F P A V L Q S S G L Y S L S S V V T V P S S S L G T Q T Y I C N V N
H K P S N T K V D K R V E P K S C D K T H T C P P C P A P E L L G G P S V F L F P P K P
K D T L M I S R T P E V T C V V V D V E H E D P E V K F N W Y V D G V E V H N A K T
K P R E E Q Y N S T Y R V V S V L T V L H Q D W L N G K E Y K C K V S N K A F P A P
I E K T I S K A K G Q P R E P Q V Y T L P P S R D E L T K N Q V S L T C L V K G F Y P S
D I A V E W E S N G Q P E N N Y K T T P P V L D S D G S F F L Y S K L T V D K S R W Q
Q G N V F S C S V M H E A L H N H Y T Q K S L S L S P G K
                                                                          SEQ ID NO: 6
2141-IgG1 - G237D/P238D/P 271G/A330R (V9) - Heavy chain
Q V Q L V Q S G A E V K K P G A S V K V S C K A S G Y T F T G Y Y M H W V R Q A P
G Q G L E W M G W I N P D S G G T N Y A Q K F Q G R V T M T R D T S I S T A Y M E L
N R L R S D D T A V Y Y C A R D Q P L G Y C T N G V C S Y F D Y W G Q G T L V T V S
S A T T K G P S V F P L A P S S K S T S G G T A A L G C L V K D Y F P E P V T V S W N
S G A L T S G V H T F P A V L Q S S G L Y S L S S V V T V P S S S L G T Q T Y I C N V N
H K P S N T K V D K R V E P K S C D K T H T C P P C P A P E L L G D D S V F L F P P K
P K D T L M I S R T P E V T C V V V D V S H E D G E V K F N W Y V D G V E V H N A K
T K P R E E Q Y N S T Y R V V S V L T V L H Q D W L N G K E Y K C K V S N K A L P R
P I E K T I S K A K G Q P R E P Q V Y T L P P S R D E L T K N Q V S L T C L V K G F Y P
S D I A V E W E S N G Q P E N N Y K T T P P V L D S D G S F F L Y S K L T V D K S R W
Q Q G N V F S C S V M H E A L H N H Y T Q K S L S L S P G K
                                                                          SEQ ID NO: 7
2141-IgG1 - G237D/P238D/H268D/P271G/A330R (V11) - Heavy chain
Q V Q L V Q S G A E V K K P G A S V K V S C K A S G Y T F T G Y Y M H W V R Q A P
G Q G L E W M G W I N P D S G G T N Y A Q K F Q G R V T M T R D T S I S T A Y M E L
N R L R S D D T A V Y Y C A R D Q P L G Y C T N G V C S Y F D Y W G Q G T L V T V S
S A T T K G P S V F P L A P S S K S T S G G T A A L G C L V K D Y F P E P V T V S W N
S G A L T S G V H T F P A V L Q S S G L Y S L S S V V T V P S S S L G T Q T Y I C N V N
H K P S N T K V D K R V E P K S C D K T H T C P P C P A P E L L G D D S V F L F P P K
P K D T L M I S R T P E V T C V V V D V S D E D G E V K F N W Y V D G V E V H N A K
T K P R E E Q Y N S T Y R V V S V L T V L H Q D W L N G K E Y K C K V S N K A L P R
P I E K T I S K A K G Q P R E P Q V Y T L P P S R D E L T K N Q V S L T C L V K G F Y P
S D I A V E W E S N G Q P E N N Y K T T P P V L D S D G S F F L Y S K L T V D K S R W
Q Q G N V F S C S V M H E A L H N H Y T Q K S L S L S P G K
                                                                          SEQ ID NO: 8
2141-IgG2 - Heavy chain
Q V Q L V Q S G A E V K K P G A S V K V S C K A S G Y T F T G Y Y M H W V R Q A P G
Q G L E W M G W I N P D S G G T N Y A Q K F Q G R V T M T R D T S I S T A Y M E L N
R L R S D D T A V Y Y C A R D Q P L G Y C T N G V C S Y F D Y W G Q G T L V T V S S
A S T K G P S V F P L A P C S R S T S E S T A A L G C L V K D Y F P E P V T V S W N S G
A L T S G V H T F P A V L Q S S G L Y S L S S V V T V P S S N F G T Q T Y T C N V D H
K P S N T K V D K T V E R K C C V E C P P C P A P P V A G P S V F L F P P K P K D T L M
I S R T P E V T C V V V D V S H E D P E V Q F N W Y V D G V E V H N A K T K P R E E Q
F N S T F R V V S V L T V V H Q D W L N G K E Y K C K V S N K G L P A P I E K T I S K
```

-continued

```
T K G Q P R E P Q V Y T L P P S R E E M T K N Q V S L T C L V K G F Y P S D I A V E W

E S N G Q P E N N Y K T T P P M L D S D G S F F L Y S K L T V D K S R W Q Q G N V F S

C S V M H E A L H N H Y T Q K S L S L S P G K
```

SEQ ID NO: 9

2141-IgG2 C127S - Heavy chain
```
Q V Q L V Q S G A E V K K P G A S V K V S C K A S G Y T F T G Y Y M H W V R Q A P G Q G L E W M G W I N P D S G G T N Y A Q K F Q G R V T M T R D T S I S T A Y M E L N R L R S D D T A V Y Y C A R D Q P L G Y C T N G V C S Y F D Y W G Q G T L V T V S S A S T K G P S V F P L A P S S R S T S E S T A A L G C L V K D Y F P E P V T V S W N S G A L T S G V H T F P A V L Q S S G L Y S L S S V V T V P S S N F G T Q T Y T C N V D H K P S N T K V D K T V E R K C C V E C P P C P A P P V A G P S V F L F P P K P K D T L M I S R T P E V T C V V V D V S H E D P E V Q F N W Y V D G V E V H N A K T K P R E E Q F N S T F R V V S V L T V V H Q D W L N G K E Y K C K V S N K G L P A P I E K T I S K T K G Q P R E P Q V Y T L P P S R E E M T K N Q V S L T C L V K G F Y P S D I A V E W E S N G Q P E N N Y K T T P P M L D S D G S F F L Y S K L T V D K S R W Q Q G N V F S

C S V M H E A L H N H Y T Q K S L S L S P G K
```

SEQ ID NO: 10

2141-IgG2 C232S - Heavy chain
```
Q V Q L V Q S G A E V K K P G A S V K V S C K A S G Y T F T G Y Y M H W V R Q A P G Q G L E W M G W I N P D S G G T N Y A Q K F Q G R V T M T R D T S I S T A Y M E L N R L R S D D T A V Y Y C A R D Q P L G Y C T N G V C S Y F D Y W G Q G T L V T V S S A S T K G P S V F P L A P C S R S T S E S T A A L G C L V K D Y F P E P V T V S W N S G A L T S G V H T F P A V L Q S S G L Y S L S S V V T V P S S N F G T Q T Y T C N V D H K P S N T K V D K T V E R K S C V E C P P C P A P P V A G P S V F L F P P K P K D T L M I S R T P E V T C V V V D V S H E D P E V Q F N W Y V D G V E V H N A K T K P R E E Q F N S T F R V V S V L T V V H Q D W L N G K E Y K C K V S N K G L P A P I E K T I S K T K G Q P R E P Q V Y T L P P S R E E M T K N Q V S L T C L V K G F Y P S D I A V E W E S N G Q P E N N Y K T T P P M L D S D G S F F L Y S K L T V D K S R W Q Q G N V F S

C S V M H E A L H N H Y T Q K S L S L S P G K
```

SEQ ID NO: 13

Signal Sequence
```
M V R L P L Q C V L W G C L L T A V H P
```

The Sequence Listing provides the sequences of the mature heavy and light chains (i.e., sequences do not include signal peptides). A signal sequence for production of the antibodies of the present invention, for example in human cells, is provided at SEQ ID NO: 13.

EQUIVALENTS

Those skilled in the art will recognize, or be able to ascertain using no more than routine experimentation, many equivalents of the specific embodiments disclosed herein. Such equivalents are intended to be encompassed by the following claims.

We claim:

1. A nucleic acid encoding the heavy and/or light chain variable region of an antibody, or antigen binding portion thereof that binds to human CD40 and comprises a heavy chain having the amino acid sequence of SEQ ID NO: 7 and a light chain having the amino acid sequence of SEQ ID NO: 2.

2. An expression vector comprising the nucleic acid of claim 1.

3. A cell transformed with an expression vector of claim 2.

4. A method of preparing an anti-human CD40 antibody, or antigen binding portion thereof, comprising:
   a) expressing the antibody, or antigen binding portion thereof, in the cell of claim 3; and
   b) isolating the antibody, or antigen binding portion thereof, from the cell.

* * * * *

UNITED STATES PATENT AND TRADEMARK OFFICE
CERTIFICATE OF CORRECTION

| | |
|---|---|
| PATENT NO. | : 11,760,805 B2 |
| APPLICATION NO. | : 17/150008 |
| DATED | : September 19, 2023 |
| INVENTOR(S) | : Jeffrey V. Ravetch et al. |

Page 1 of 1

It is certified that error appears in the above-identified patent and that said Letters Patent is hereby corrected as shown below:

In the Specification

Column 1, Line 12, please add the following Federal Funding paragraph:
--STATEMENT OF GOVERNMENT FUNDING
This invention was made with government support under grant no. HHSN261200800001E awarded by the National Institutes of Health. The government has certain rights in the invention.--

Signed and Sealed this
Seventh Day of November, 2023

Katherine Kelly Vidal
*Director of the United States Patent and Trademark Office*

SEQUENCE LISTING

```
<160> NUMBER OF SEQ ID NOS: 15

<210> SEQ ID NO 1
<211> LENGTH: 456
<212> TYPE: PRT
<213> ORGANISM: Homo sapiens
```

```
<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Thr Ala Val Tyr Tyr Cys
                85                  90                  95

Ala Arg Asp Gln Pro Leu Gly Tyr Cys Thr Asn Gly Val Cys Ser Tyr
                100                 105                 110

Phe Asp Tyr Trp Gly Gln Gly Thr Leu Val Thr Val Ser Ser Ala Thr
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400
```

-continued

```
Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Tyr Ser Trp
            20                  25                  30

Leu Ala Trp Tyr Gln Gln Lys Pro Gly Lys Ala Pro Asn Leu Leu Ile
        35                  40                  45

Tyr Thr Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ile Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 456
<212> TYPE: PRT
<213> ORGANISM: Artificial Sequence
<220> FEATURE:
<223> OTHER INFORMATION: synthetic sequence

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

-continued

```
Tyr Met His Trp Val Arg Gln Ala Pro Gly Gln Gly Leu Glu Trp Met
         35                  40                  45

Gly Trp Ile Asn Pro Asp Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Asn Arg Leu Arg Ser Asp Asp Thr Ala Val Tyr Tyr Cys
                 85                  90                  95

Ala Arg Asp Gln Pro Leu Gly Tyr Cys Thr Asn Gly Val Cys Ser Tyr
                100                 105                 110

Phe Asp Tyr Trp Gly Gln Gly Thr Leu Val Thr Val Ser Ser Ala Thr
                115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Ser Leu Gly Thr Gln Thr Tyr Ile
                195                 200                 205

Cys Asn Val Asn His Lys Pro Ser Asn Thr Lys Val Asp Lys Arg Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Ala Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430
```

Ser Cys Ser Val Met His Glu Ala Leu His Asn His Tyr Thr Gln Lys
         435                 440                 445

Ser Leu Ser Leu Ser Pro Gly Lys
    450                 455

<210> SEQ ID NO 4
<211> LENGTH: 456
<212> TYPE: PRT
<213> ORGANISM: Artificial Sequence
<220> FEATURE:
<223> OTHER INFORMATION: synthetic sequence

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Thr
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Glu His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

```
Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 5
<211> LENGTH: 456
<212> TYPE: PRT
<213> ORGANISM: Artificial Sequence
<220> FEATURE:
<223> OTHER INFORMATION: synthetic sequence

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Thr
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240
```

```
Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Glu His Glu Asp Pro Glu Val Lys Phe Asn Trp Tyr Val
                275                 280                 285

Asp Gly Val Glu Val His Asn Ala Lys Thr Lys Pro Arg Glu Glu Gln
                290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Phe Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
                370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
                435                 440                 445

Ser Leu Ser Leu Ser Pro Gly Lys
                450                 455

<210> SEQ ID NO 6
<211> LENGTH: 456
<212> TYPE: PRT
<213> ORGANISM: Artificial Sequence
<220> FEATURE:
<223> OTHER INFORMATION: synthetic sequence

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
                35                  40                  45

Gly Trp Ile Asn Pro Asp Ser Gly Gly Thr Asn Tyr Ala Gln Lys Phe
                50                  55                  60

Gln Gly Arg Val Thr Met Thr Arg Asp Thr Ser Ile Ser Thr Ala Tyr
65              70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
                100                 105                 110

Phe Asp Tyr Trp Gly Gln Gly Thr Leu Val Thr Val Ser Ser Ala Thr
                115                 120                 125

Thr Lys Gly Pro Ser Val Phe Pro Leu Ala Pro Ser Ser Lys Ser Thr
                130                 135                 140
```

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
210                 215                 220

Glu Pro Lys Ser Cys Asp Lys Thr His Thr Cys Pro Pro Cys Pro Ala
225                 230                 235                 240

Pro Glu Leu Leu Gly Asp Asp Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Gly Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Arg Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
        450                 455

<210> SEQ ID NO 7
<211> LENGTH: 456
<212> TYPE: PRT
<213> ORGANISM: Artificial Sequence
<220> FEATURE:
<223> OTHER INFORMATION: synthetic sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

```
Gly Trp Ile Asn Pro Asp Ser Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Thr
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Asp Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Asp Glu Asp Gly Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Arg Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

```
<210> SEQ ID NO 8
<211> LENGTH: 452
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
                85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380
```

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 9
<211> LENGTH: 452
<212> TYPE: PRT
<213> ORGANISM: Artificial Sequence
<220> FEATURE:
<223> OTHER INFORMATION: synthetic sequence

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Trp Ile Asn Pro Asp Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Asn Arg Leu Arg Ser Asp Asp Thr Ala Val Tyr Tyr Cys
            85                  90                  95

Ala Arg Asp Gln Pro Leu Gly Tyr Cys Thr Asn Gly Val Cys Ser Tyr
            100                 105                 110

Phe Asp Tyr Trp Gly Gln Gly Thr Leu Val Thr Val Ser Ser Ala Ser
            115                 120                 125

Thr Lys Gly Pro Ser Val Phe Pro Leu Ala Pro Ser Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
            195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
            275                 280                 285

```
Val His Asn Ala Lys Thr Lys Pro Arg Glu Glu Gln Phe Asn Ser Thr
    290                 295                 300
Phe Arg Val Val Ser Val Leu Thr Val Val His Gln Asp Trp Leu Asn
305                 310                 315                 320
Gly Lys Glu Tyr Lys Cys Lys Val Ser Asn Lys Gly Leu Pro Ala Pro
                325                 330                 335
Ile Glu Lys Thr Ile Ser Lys Thr Lys Gly Gln Pro Arg Glu Pro Gln
            340                 345                 350
Val Tyr Thr Leu Pro Pro Ser Arg Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Met Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 10
<211> LENGTH: 452
<212> TYPE: PRT
<213> ORGANISM: Artificial Sequence
<220> FEATURE:
<223> OTHER INFORMATION: synthetic sequence

<400> SEQUENCE: 10

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Gly Tyr
            20                  25                  30
Tyr Met His Trp Val Arg Gln Ala Pro Gly Gln Gly Leu Glu Trp Met
        35                  40                  45
Gly Trp Ile Asn Pro Asp Ser Gly Gly Thr Asn Tyr Ala Gln Lys Phe
    50                  55                  60
Gln Gly Arg Val Thr Met Thr Arg Asp Thr Ser Ile Ser Thr Ala Tyr
65                  70                  75                  80
Met Glu Leu Asn Arg Leu Arg Ser Asp Thr Ala Val Tyr Tyr Cys
                85                  90                  95
Ala Arg Asp Gln Pro Leu Gly Tyr Cys Thr Asn Gly Val Cys Ser Tyr
            100                 105                 110
Phe Asp Tyr Trp Gly Gln Gly Thr Leu Val Thr Val Ser Ser Ala Ser
        115                 120                 125
Thr Lys Gly Pro Ser Val Phe Pro Leu Ala Pro Cys Ser Arg Ser Thr
    130                 135                 140
Ser Glu Ser Thr Ala Ala Leu Gly Cys Leu Val Lys Asp Tyr Phe Pro
145                 150                 155                 160
Glu Pro Val Thr Val Ser Trp Asn Ser Gly Ala Leu Thr Ser Gly Val
                165                 170                 175
His Thr Phe Pro Ala Val Leu Gln Ser Ser Gly Leu Tyr Ser Leu Ser
            180                 185                 190
```

```
Ser Val Val Thr Val Pro Ser Ser Asn Phe Gly Thr Gln Thr Tyr Thr
            195                 200                 205

Cys Asn Val Asp His Lys Pro Ser Asn Thr Lys Val Asp Lys Thr Val
            210                 215                 220

Glu Arg Lys Ser Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
            290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
            325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 11
<211> LENGTH: 277
<212> TYPE: PRT
<213> ORGANISM: Homo sapiens

<400> SEQUENCE: 11

Met Val Arg Leu Pro Leu Gln Cys Val Leu Trp Gly Cys Leu Leu Thr
1               5                   10                  15

Ala Val His Pro Glu Pro Pro Thr Ala Cys Arg Glu Lys Gln Tyr Leu
            20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
        50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
            85                  90                  95
```

```
Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
    210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
            260                 265                 270

Val Gln Glu Arg Gln
            275

<210> SEQ ID NO 12
<211> LENGTH: 261
<212> TYPE: PRT
<213> ORGANISM: Homo sapiens

<400> SEQUENCE: 12

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175
```

```
Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 13
<211> LENGTH: 20
<212> TYPE: PRT
<213> ORGANISM: Homo sapiens

<400> SEQUENCE: 13

Met Val Arg Leu Pro Leu Gln Cys Val Leu Trp Gly Cys Leu Leu Thr
1               5                   10                  15

Ala Val His Pro
            20

<210> SEQ ID NO 14
<211> LENGTH: 222
<212> TYPE: PRT
<213> ORGANISM: Artificial
<220> FEATURE:
<223> OTHER INFORMATION: Synthetic

<400> SEQUENCE: 14

Cys Pro Pro Cys Pro Ala Pro Glu Leu Leu Gly Asp Asp Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser Asp Glu Asp Gly Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Arg Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190
```

```
Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 15
<211> LENGTH: 218
<212> TYPE: PRT
<213> ORGANISM: Artificial
<220> FEATURE:
<223> OTHER INFORMATION: Synthetic

<400> SEQUENCE: 15

Pro Ala Pro Glu Leu Leu Gly Asp Asp Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Asp Glu Asp Gly Glu Val Lys Phe Asn Trp
        35                  40                  45

Tyr Val Asp Gly Val Glu Val His Asn Ala Lys Thr Lys Pro Arg Glu
    50                  55                  60

Glu Gln Tyr Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Arg Pro Ile Glu Lys Thr Ile Ser Lys Ala Lys Gly
            100                 105                 110

Gln Pro Arg Glu Pro Gln Val Tyr Thr Leu Pro Pro Ser Arg Asp Glu
        115                 120                 125

Leu Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215
```